(12) United States Patent  (10) Patent No.: US 7,942,826 B1
Scholl et al.  (45) Date of Patent: May 17, 2011

(54) INSULATED PEDICLE ACCESS SYSTEM AND RELATED METHODS

(75) Inventors: Thomas Scholl, San Diego, CA (US); Albert Kim, San Diego, CA (US); Jared Arambula, San Diego, CA (US); Scot Martinelli, San Diego, CA (US); Eric Finley, Lancaster, CA (US); Albert Pothier, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1177 days.

(21) Appl. No.: 11/448,237

(22) Filed: Jun. 6, 2006

Related U.S. Application Data

(60) Provisional application No. 60/687,947, filed on Jun. 6, 2005.

(51) Int. Cl.
   *A61B 5/05* (2006.01)
(52) U.S. Cl. .......................................... 600/554
(58) Field of Classification Search .......... 600/562–567, 600/554, 547; 606/79, 80, 167; 604/263, 604/198; 607/116
See application file for complete search history.

(56) References Cited

U.S. PATENT DOCUMENTS

| | | | |
|---|---|---|---|
| 3,540,447 A | 11/1970 | Howe | |
| 3,595,230 A | 7/1971 | Suyeoka et al. | |
| 3,598,108 A | 8/1971 | Jamshidi et al. | |
| 3,850,158 A | 11/1974 | Elias et al. | |
| 4,230,123 A | 10/1980 | Hawkins et al. | |
| 4,256,119 A | 3/1981 | Gauthier | |
| 4,262,676 A | 4/1981 | Jamshidi | |
| 4,266,555 A | 5/1981 | Jamshidi | |
| 4,314,565 A | 2/1982 | Lee | |
| 4,356,828 A | 11/1982 | Jamshidi | |
| 4,592,369 A | 6/1986 | Davis et al. | |
| 4,609,370 A | 9/1986 | Morrison | |
| 4,630,616 A | 12/1986 | Tretinyak | |
| 4,702,738 A | 10/1987 | Spencer | |
| 4,759,377 A | 7/1988 | Dykstra | |
| 4,775,369 A * | 10/1988 | Schwartz ...................... 604/263 |

(Continued)

FOREIGN PATENT DOCUMENTS

EP  0607688  7/1994

(Continued)

OTHER PUBLICATIONS

"Brackman II EMG System", *Medical Electronics*, 1994, 4pages.

(Continued)

*Primary Examiner* — Max Hindenburg
*Assistant Examiner* — Brian Szmal
(74) *Attorney, Agent, or Firm* — Jonathan Spangler; Rory Schermerhorn

(57) ABSTRACT

A pedicle access system including a cannula, a stylet, and a removable T-handle. The pedicle access system may be used to percutaneously approach the pedicle, initiate pilot hole formation, and conduct a stimulation signal to the target site for the purposes of performing a pedicle integrity assessment during the pilot hole formation. To do this, the cannula and stylet are locked in combination and inserted through an operating corridor to the pedicle target site, using the T-handle to facilitate easy movement and positioning of the cannula/stylet combination. A stimulation signal may be applied during pilot hole formation to conduct the pedicle integrity assessment. In a significant aspect, the T-handle may be detached from the cannula/stylet combination to facilitate the use of various surgical tools as necessary.

31 Claims, 28 Drawing Sheets

U.S. PATENT DOCUMENTS

| | | | |
|---|---|---|---|
| 4,793,363 | A | 12/1988 | Ausherman et al. |
| 4,838,282 | A | 6/1989 | Strasser et al. |
| 4,964,411 | A | 10/1990 | Johnson et al. |
| 5,147,327 | A | 9/1992 | Johnson |
| 5,151,089 | A | 9/1992 | Kirk et al. |
| 5,196,015 | A | 3/1993 | Neubardt |
| 5,201,721 | A | 4/1993 | Lee et al. |
| 5,242,418 | A | 9/1993 | Weinstein |
| 5,279,584 | A | 1/1994 | Dillard et al. |
| 5,357,974 | A | 10/1994 | Baldridge |
| 5,368,046 | A | 11/1994 | Scarfone et al. |
| 5,415,645 | A | 5/1995 | Friend et al. |
| 5,474,558 | A | 12/1995 | Neubardt |
| 5,480,440 | A | 1/1996 | Kambin |
| 5,549,656 | A | 8/1996 | Reiss |
| 5,645,076 | A | 7/1997 | Yoon |
| 5,758,655 | A | 6/1998 | Como et al. |
| 5,807,275 | A | 9/1998 | Jamshidi |
| 5,928,162 | A | 7/1999 | Giurtino et al. |
| 5,928,163 | A | 7/1999 | Roberts et al. |
| 6,033,369 | A | 3/2000 | Goldenberg |
| 6,038,477 | A | 3/2000 | Kayyali |
| 6,063,037 | A * | 5/2000 | Mittermeier et al. ......... 600/567 |
| 6,104,960 | A | 8/2000 | Duysens et al. |
| 6,110,128 | A | 8/2000 | Andelin et al. |
| 6,181,961 | B1 | 1/2001 | Prass et al. |
| 6,221,029 | B1 | 4/2001 | Mathis et al. |
| 6,261,241 | B1 | 7/2001 | Burbank et al. |
| 6,302,852 | B1 | 10/2001 | Fleming et al. |
| 6,306,100 | B1 | 10/2001 | Prass et al. |
| 6,312,394 | B1 | 11/2001 | Fleming |
| 6,340,351 | B1 | 1/2002 | Goldenberg |
| 6,468,279 | B1 | 10/2002 | Reo |
| 6,475,190 | B2 | 11/2002 | Young |
| 6,554,778 | B1 | 4/2003 | Fleming |
| 6,579,244 | B2 | 6/2003 | Goodwin |
| 6,623,437 | B2 | 9/2003 | Hinchliffe et al. |
| 6,719,692 | B2 | 4/2004 | Kleffner et al. |
| D489,456 | S | 5/2004 | Groenke et al. |
| 6,796,985 | B2 | 9/2004 | Bolger et al. |
| 6,819,956 | B2 | 11/2004 | DiLorenzo |
| 6,849,047 | B2 | 2/2005 | Goodwin |
| 6,855,105 | B2 | 2/2005 | Jackson et al. |
| 6,875,183 | B2 | 4/2005 | Cervi |
| 6,929,606 | B2 | 8/2005 | Ritland |
| 7,018,343 | B2 | 3/2006 | Plishka |
| 7,063,703 | B2 | 6/2006 | Reo |
| 7,081,123 | B2 | 7/2006 | Merboth et al. |
| 7,089,059 | B1 | 8/2006 | Pless |
| 7,399,306 | B2 | 7/2008 | Reiley et al. |
| 7,468,041 | B2 | 12/2008 | Rhodes et al. |
| 7,468,042 | B2 | 12/2008 | Turovskiy et al. |
| 7,470,236 | B1 | 12/2008 | Kelleher et al. |
| 2001/0029387 | A1 | 10/2001 | Wolf |
| 2002/0072688 | A1 | 6/2002 | Burbank et al. |
| 2003/0191414 | A1 | 10/2003 | Reiley et al. |
| 2004/0225228 | A1 | 11/2004 | Ferree |
| 2005/0033380 | A1 | 2/2005 | Tanner et al. |
| 2005/0192575 | A1 | 9/2005 | Pacheco |
| 2005/0203441 | A1 | 9/2005 | Voegele |
| 2006/0025703 | A1 * | 2/2006 | Miles et al. ................ 600/554 |
| 2006/0173521 | A1 * | 8/2006 | Pond et al. ................ 607/116 |
| 2007/0083167 | A1 | 4/2007 | Smith et al. |
| 2007/0197935 | A1 | 8/2007 | Reiley et al. |
| 2007/0260184 | A1 | 11/2007 | Justis et al. |
| 2007/0260255 | A1 | 11/2007 | Haddock et al. |
| 2008/0071302 | A1 | 3/2008 | Castillo et al. |
| 2008/0228104 | A1 | 9/2008 | Uber et al. |
| 2009/0194446 | A1 | 8/2009 | Miller et al. |

FOREIGN PATENT DOCUMENTS

| | | |
|---|---|---|
| EP | 0754431 | 1/1997 |
| WO | WO 99/56631 | 11/1999 |
| WO | WO 01/37728 | 5/2001 |
| WO | WO 03037170 A2 * | 5/2003 |
| WO | WO 2005013805 A2 * | 2/2005 |

OTHER PUBLICATIONS

"Neurovision SE Nerve Locator /Monitor", RLN Systems. Inc. Operators Manual, 1999, 22 pages.

"The Brackman II EMG Monitoring System", *Medical Electronics Co. Operator's Manual Version 1.1*, 1995, 50 pages.

"The Nicolet Viking IV", Nicolet Biomedical Products 1999, 6 pages.

"NIM-Spine System Neural Integrity Monitor," *Medtronic Sofamor Danek USA*, 2004, 2 pages.

Anderson, D. G. et al., "Pedicle screws with high electrical resistance: a potential source of error with stimulus-evoked EMG", *Spine*. 27(14): Department of Orthopaedic Surgery, University of Virginia Jul. 15, 2002, 1577-1581.

Bose, Bikash et al., "Neurophysiologic Monitoring of Spinal Nerve Root Function During Instrumented Posterior Lumbar Spine Surgery", *Spine*, 27(13) 2002, 1444-1450.

Calancie, Blair et al., "Stimulus-Evoked EMG Monitoring During Transpedicular Lumbosacral Spine Instrumentation", *Spine*, 19(24), 1994, pp. 2780-2786.

Clements, David et al., "Evoked and Spontaneous Electromyography to Evaluate Lumbosacral Pedicle Screw Placement", *Spine*, 21(5),1996, 600-604.

Danesh-Clough, T. et al., "The use of evoked EMG in detecting misplaced thoracolumbar pedicle screws", *Spine*. 26(12) Orthopaedic Department, Dunedin Hospital Jun. 15, 2001, 1313-1316.

Darden, B. V. et al., "A comparison of impedance and electromyogram measurements in detecting the presence of pedicle wall breakthrough", *Spine*. 23(2) Charlotte Spine Center, North Carolina Jan. 15, 1998, 256-262.

Ebraheim, N. A. et al., "Anatomic relations between the lumbar pedicle and the adjacent neural structures", *Spine*. 22(20) Department of Orthopaedic Surgery, Medical College of Ohio, Oct. 15, 1997, 2338-2341.

Glassman, Steven et al., "A Prospective Analysis of Intraoperative Electromyographic Monitoring of Pedicle Screw placement With Computed Tomographic Scan Confirmation", *Spine*, 20(12) 1995, 1375-1379.

Holland, N. R. et al., "Higher electrical stimulus intensities are required to activate chronically compressed nerve roots. Implications for intraoperative electromyographic pedicle screw testing", *Spine*. 23(2) Department of Neurology, Johns Hopkins University School of Medicine Jan. 15, 1998, 224-227.

Holland, Neil et al., "Intraoperative Electromyography During Thoracolumbar Spinal Surgery", *Spine*, 23(17) 1998, 1915-1922.

Journee, H. L. et al., "System for Intra-Operative Monitoring of the Cortical Integrity of the Pedicle During Screw Placement in Low-Back Surgery: Design and Clinical Results", *Sensory and neuromuscular diagnostic instrumentation and data analysis, 18th Annual international Conference on Engineering in Medicine and Biology Society*, 1(31) Oct. 1996, 144-145.

Lenke, Lawrence et al., "Triggered Electromyographic Threshold for Accuracy of Pedicle Screw Placement", *Spine*, 20 (14) 1995, 1585-1591.

Maguire, J. et al., "Evaluation of Intrapedicular Screw Position Using Intraoperative Evoked Electromyography", *Spine*, 20(9) 1995, 1068-1074.

Minahan, R. E. et al., "The effect of neuromuscular blockade on pedicle screw stimulation thresholds", Spine. 25(19) Department of Neurology, Johns Hopkins University, School of Medicine, Oct. 1, 2000, 2526-2530.

Toleikis, J. et al., "The Usefulness of Electrical Stimulation for Assessing Pedicle Screw Replacements", *Journal of Spinal Disorder*, 13(4) 2000, 283-289.

Welch et al., "Evaluation with evoked and spontaneous electromyography during lumbar instrumentation : a prospective study", *J. Neurosurg* 87 Sep. 1997, 397-402.

* cited by examiner

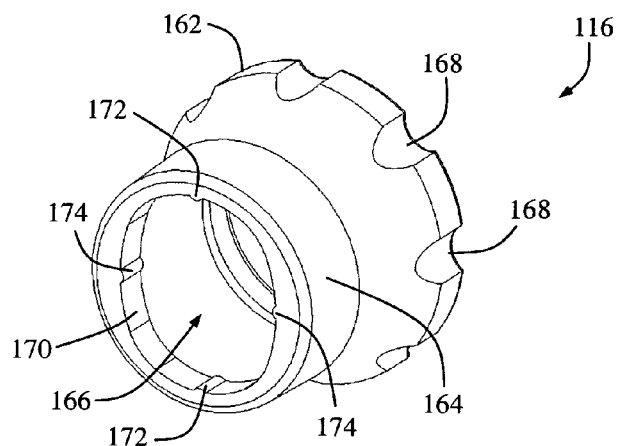
FIG. 28
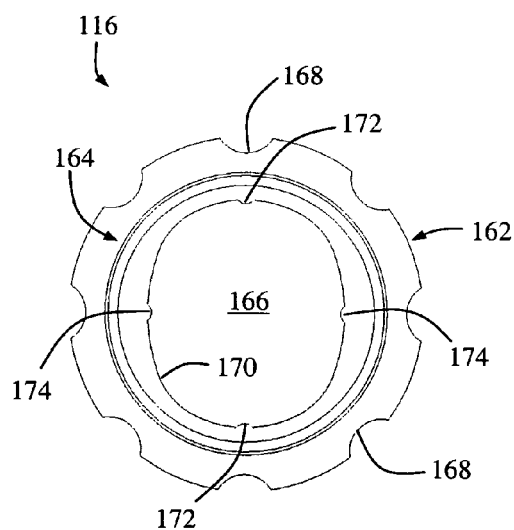 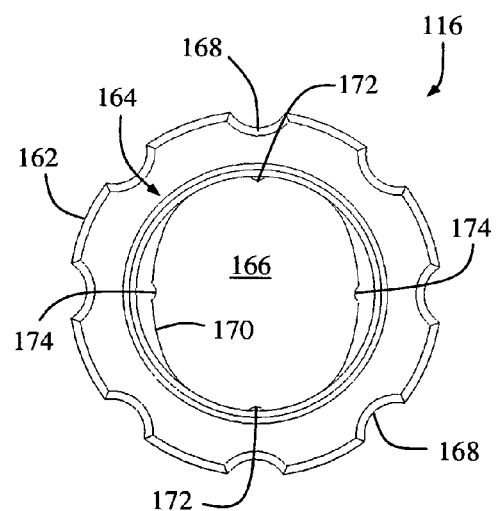
FIG. 29  FIG. 30

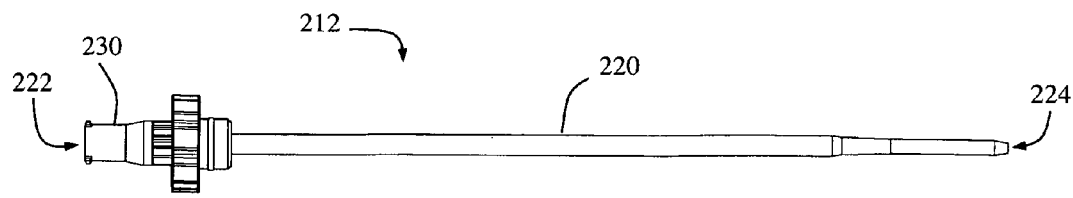
FIG. 35
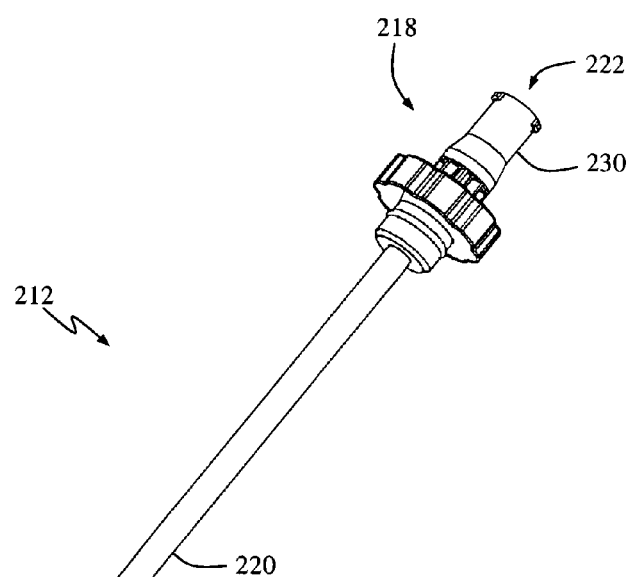
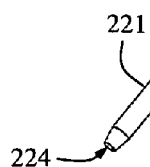
FIG. 36

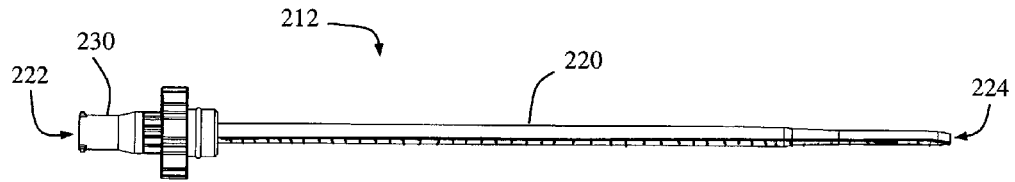
FIG. 52
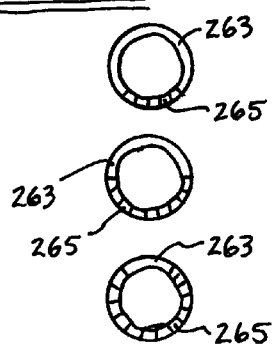
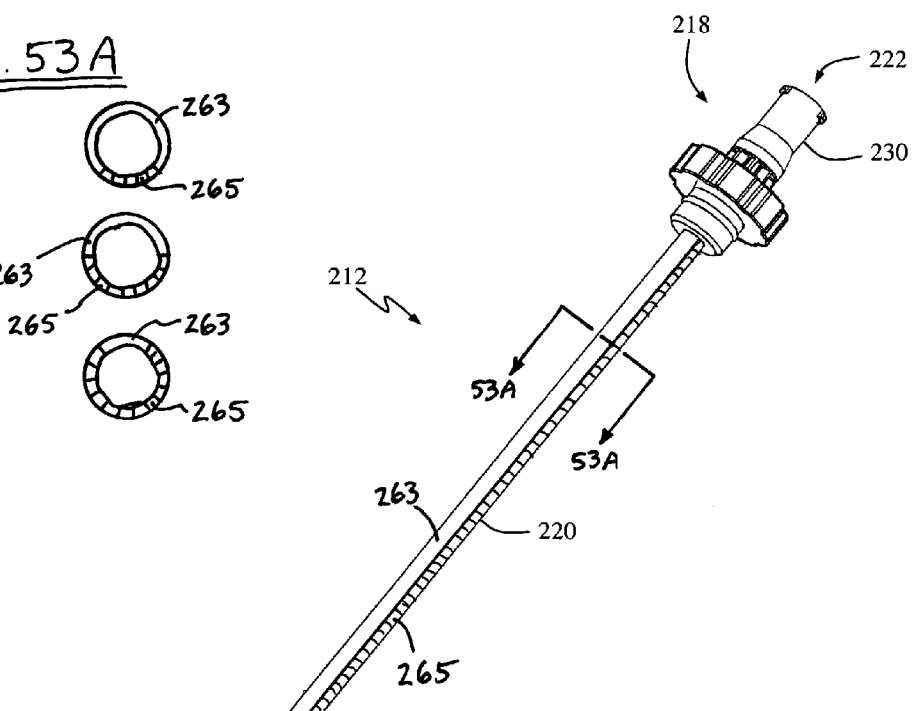
FIG. 53

INSULATED PEDICLE ACCESS SYSTEM AND RELATED METHODS

CROSS-REFERENCES TO RELATED APPLICATIONS

The present application is a non-provisional patent application claiming benefit under 35 U.S.C. §119(e) from U.S. Provisional Application Ser. No. 60/687,947, filed on Jun. 6, 2005, the entire contents of which are hereby expressly incorporated by reference into this disclosure as if set forth fully herein.

BACKGROUND OF THE INVENTION

I. Field of the Invention

The present invention relates to a system and methods aimed at accessing a pedicle in preparation for the placement of pedicle screws.

II. Discussion of the Prior Art

An emerging trend in spinal surgery is to perform surgery in a minimally invasive or minimal access fashion to avoid the trauma of so-called open or "direct access" procedures. A specific area of interest is in the placement of pedicle screws, which are typically employed to effect posterior fixation in spinal fusion procedures. While great strides are being made in this area, a risk exists (as it does in open procedures) that the pedicle may become breached, cracked, or otherwise compromised during the procedure. If the pedicle (or more specifically, the cortex of the medial wall, lateral wall, superior wall and/or inferior wall) is breached, cracked, or otherwise compromised, the patient may experience pain or neurologic deficit due to unwanted contact between the pedicle screw and exiting nerve roots. This often necessitates revision surgery, which can be painful and costly, both in terms of recovery time and hospitalization.

Some attempts to minimize the risk of a pedicle breach involve capitalizing on the insulating characteristics of bone and the conductivity of the exiting nerve roots themselves to perform pedicle integrity assessments. That is, if the wall of the pedicle is breached, a stimulation signal applied to the pedicle screw and/or the pilot hole (prior to screw introduction) will cause the various muscle groups coupled to the exiting nerve roots to contract. If the pedicle wall has not been breached, the insulating nature of the pedicle will prevent the stimulation signal from innervating the given nerve roots such that the associated muscle groups will twitch at a higher stimulation level. Traditional EMG monitoring systems may be employed to augment the ability to detect such innervation.

One period during a pedicle screw procedure in which the risk of a pedicle breach is prevalent is during the initial access of the pedicle. Typically, initial access to a pedicle may be achieved by inserting a needle to the target site and driving the needle point into the pedicle, creating a pilot hole. Due to the size and shape of the typical needle, however, manipulation and maneuvering of the needle may be awkward or difficult, increasing the risk of complication. Additionally, the pedicle may be breached and nerve damage done during the initial drive of the needle into the pedicle, before a pedicle integrity test assessment may be performed.

A problem that may arise when various medical instruments are electrified and used with traditional EMG monitoring systems is that different instruments may produce different EMG stimulation thresholds. For example, an electrified needle may exhibit a threshold stimulation of approximately 5-6 mA, while a bone screw placed in the same location may exhibit a threshold stimulation of approximately 16-20 mA. This can be problematic in that an electrified needle may tend to indicate a breach in the pedicle wall when in fact the pedicle wall is intact.

The present invention is directed at eliminating, or at least improving upon, the shortcomings of the prior art.

SUMMARY OF THE INVENTION

The present invention provides a pedicle access system that facilitates ease of handling and can achieve dynamic pedicle integrity testing while forming a pilot hole.

According to a broad aspect of the present invention the pedicle access system includes a cannula, a stylet, and a removable T-handle. The pedicle access system of the present invention may be used to percutaneously approach the pedicle, initiate pilot hole formation, and conduct a stimulation signal to the target site for the purposes of performing a pedicle integrity assessment during the pilot hole formation. To do this, the cannula and stylet are locked in combination and inserted through an operating corridor to the pedicle target site, using the T-handle to facilitate easy movement and positioning of the cannula/stylet combination. A stimulation signal may be applied during pilot hole formation to conduct the pedicle integrity assessment. In a significant aspect of the present invention, the T-handle may be detached from the cannula/stylet combination to facilitate the use of various surgical tools as necessary.

The cannula includes a coupling element and an elongated shaft. An interior lumen extends through the cannula from a first opening in the coupling element to a second opening in the distal region of the elongated shaft. The elongated shaft may be composed of a conductive material, such as metal. A polymeric coating blankets or otherwise encapsulates a majority of the exterior surface of the elongated shaft, such that the elongated shaft includes an insulated region and an uninsulated region. The elongated shaft may incorporate one or more diameter changes along its length.

The coupling element comprises three sections. First, a proximal region is dimensioned to engage with the stylet. The proximal region may also include at least one tab member protruding in a generally lateral direction. The tab member functions to lock the cannula and stylet in position together. Second, a center section is dimensioned to engage with the T-handle. At least one cutout may be provided in the exterior surface of the center section. The cutout functions to secure the T-handle to the cannula/stylet combination, or optionally to the cannula only. Finally, there is a base portion having a circumference greater than that of the center section such that a ledge is formed at the interface of the center section and the base portion.

The stylet comprises a locking cap and a needle element. The locking cap has a similar size and shape as the center section. The locking cap contains a generally cylindrical aperture dimensioned to receive the generally cylindrical top section of the cannula. Furthermore, the locking cap includes at least one longitudinal channel and at least one lateral channel that interact with the tab member as a means to secure the stylet and cannula in place.

The longitudinal channel has a length dimension corresponding to the length of the generally cylindrical aperture and a width dimension sufficient to accommodate the length of the tab member. The lateral channel extends generally perpendicularly from the proximal end of the longitudinal channel, such that together the channels form a generally half-T shape. The longitudinal channel and the lateral channel, along with a ridge positioned on at least one edge of the lateral channel interact with the tab member on the cannula to lock the stylet and cannula together. Additionally, the locking cap may include a ramped surface to facilitate engagement with the T-handle.

The proximal portion of the needle element may be attached to the interior of the locking cap. The elongated shaft of the needle element extends distally from the proximal portion, with a significant portion protruding from the opening of the generally cylindrical aperture. The needle element is dimensioned to be inserted through the interior lumen of the cannula. When fully inserted, a distal portion of the needle element may protrude slightly from the bottom opening of the cannula. The needle element may be composed of a conductive material, such as metal, or a non-conductive material with one or more embedded conductive elements at or near the distal end capable of being communicatively linked with a pedicle integrity testing system.

To combine the cannula and stylet, the needle element is inserted into the interior lumen of the cannula through the opening in the coupling element. The locking cap is positioned such that its longitudinal channels are aligned with the tab members of the cannula. The proximal region of the cannula is received into the aperture on the locking cap, and the tab members pass through the longitudinal channels. Insertion is complete when the proximal region is fully received by the aperture, leaving the locking cap in an "unlocked" position. In the unlocked position, the tab members are positioned at the proximal ends of the longitudinal channels. In this position the locking cap and center section of the cannula are not aligned. To lock the stylet in place in the cannula, the locking cap is rotated until it is aligned with the center section. As the lateral channels rotate around the tab members, the ridges may be deformed when they contact the tab members. When the locking cap and center section align, the ridges may clear the tab members and regain their original forms, thereby preventing inadvertent rotation back to the unlocked position.

The T-handle includes a grip region, an aperture for engaging the cannula or cannula/stylet combination, and a locking mechanism for securing the T-handle to the cannula. The T-handle aperture is dimensioned to snugly receive both the locking cap and the center section of the cannula when they are aligned in the locked position. The locking mechanism preferably comprises a lever having one end integrated into the aperture wall and a free end extending therefrom. The majority of the lever (excluding the free end) may be the same thickness as the aperture wall and does not protrude, interiorly or exteriorly, from the aperture wall. In its "natural" state, the free end does protrude into the aperture space. The free end is dimensioned to engage the cutout in the center section of the cannula. The interior surface of the free end may be slightly ramped. The ramped portion works in concert with the ramped surface of the locking cap to force the free end out of its natural state so the locking cap and the center section can fit into the T-handle aperture. When the locking cap and center section are fully inserted into the T-handle aperture, the locking mechanism aligns with the cutout in the cannula, returns to its natural state, and locks the T-handle to the cannula. Optionally, the T-handle may be cannulated.

In an alternative aspect of the present invention, the pedicle access system may be provided with a stylet, a cannula and a lock collar. Any part of the stylet and/or cannula may be coated with a nonconductive insulative coating to prevent shunting of electrical current.

In a further alternative aspect of the present invention, the pedicle access system may be provided with a retractable insulation sheath dimensioned to cover the electrically conductive cannula and stylet needle. The retractable insulation sheath is adapted to electrically insulate the pedicle access system as it is advanced along an operative corridor to a bony structure. As the needle element is introduced into the bony structure (e.g. a pedicle) during pilot hole formation, the insulation sheath retracts to remain outside the bone and prevent electrical current intended for the pilot hole from shunting to surrounding tissue.

In a significant aspect of the present invention, the pedicle access system may be used in combination with neurophysiology monitoring systems and methods to conduct pedicle integrity assessments while achieving initial access to the pedicle and forming a pilot hole. The neurophysiology system performs pedicle integrity assessments by determining the amount of electrical communication between a stimulation signal and the adjacent nerve root. The pedicle access system may be coupled with the neurophysiology system by attaching an electric coupling device to the uninsulated region of the cannula.

In another significant aspect of the present invention, the pedicle access system may be used in cooperation with spinal fixation systems that require access to pedicle target sites and need pilot holes, as the cannula may be used to guide parts of the surgical fixation system to the target site.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 28-30 are perspective, top plan and bottom plan views, respectively, of a lock collar forming part of the pedicle access system of FIG. 20;

FIGS. 35-36 are side and perspective views, respectively, of a cannula forming part of the pedicle access system of FIG. 31;

FIGS. 52-53 are side and perspective views, respectively, of a cannula forming part of the pedicle access system of FIG. 51;

FIG. 53A are cross-sectional views taken along lines 53A-53A in FIG. 53 illustrating the relative size of the insulated and non-insulated regions of the cannula of FIGS. 51-53.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The insulated pedicle access system and related methods disclosed herein boast a variety of inventive features and components that warrant patent protection, both individually and in combination.

Figure 1:
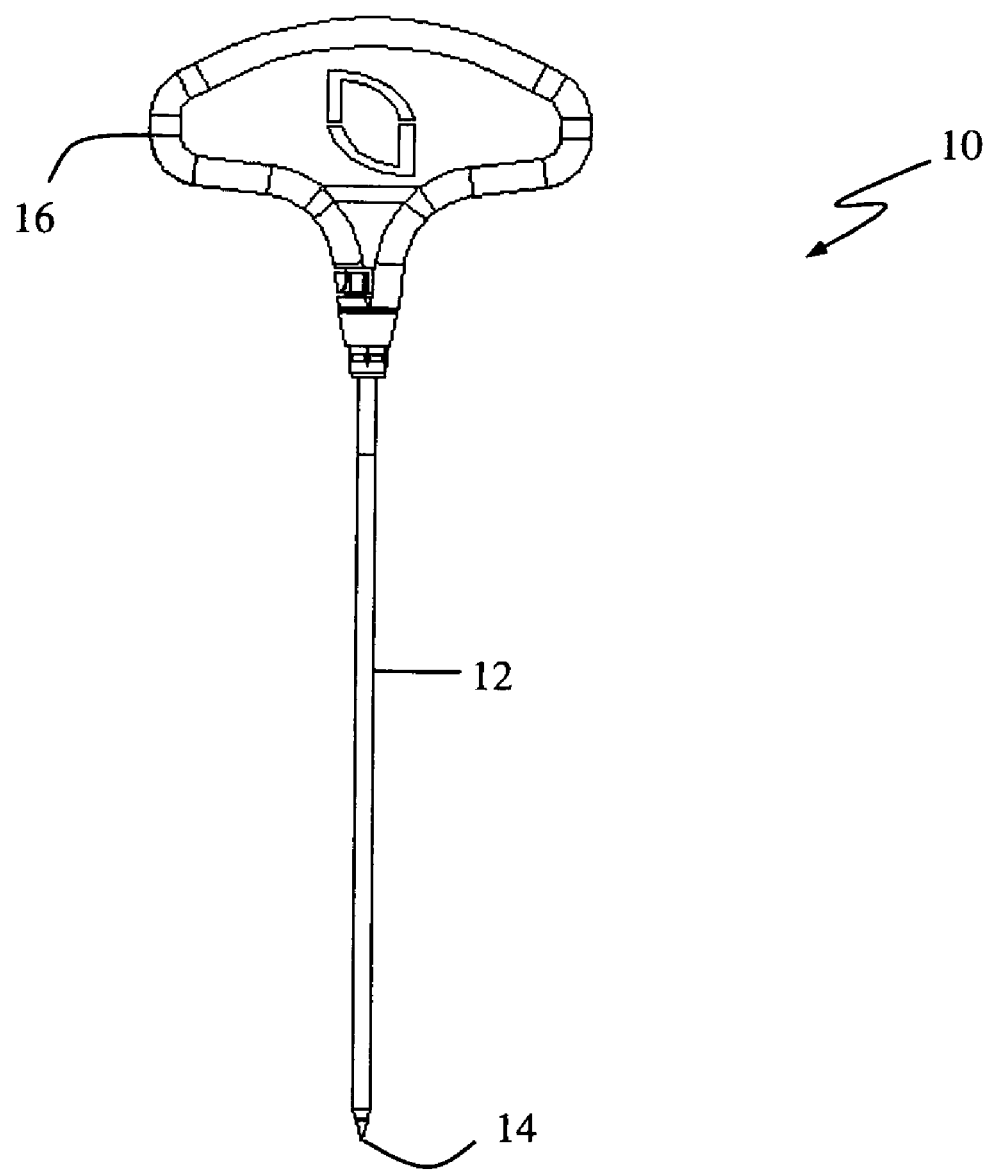
FIG. 1 is a plan view of an example of a pedicle access system according to one embodiment of the present invention.

FIG. 1 illustrates an example of a pedicle access system 10 according to one embodiment of the present invention. The pedicle access system 10 includes a cannula 12, a stylet 14, and a T-handle 16. As will be described with greater detail below, the pedicle access system 10 may be used in conjunction with a neurophysiologic monitoring system (as described herein or otherwise commercially available) to percutaneously approach the pedicle, initiate pilot hole formation, and conduct a stimulation signal to the target site for the purposes of performing a pedicle integrity assessment during formation of the pilot hole. To do this, the cannula 12 and stylet 14 may be lockingly mated to form a cannula/stylet combination 15 (e.g. FIG. 9) which may be inserted through an operating corridor to the pedicle target site, using the T-handle 16 to facilitate easy movement and positioning of the cannula/stylet combination 15. The cannula/stylet combination 15 may be driven into the bone at the target site to form a pilot hole while a stimulation signal is applied to the pedicle access system 10 and conducted to the target site to assess the integrity of the pedicle during hole formation. The T-handle 16 may be detached from the cannula/stylet combination 15 to facilitate the use of various surgical tools (such as by way of example only a forceps, mallet, or needle driver) after proper positioning of the cannula 12 and stylet 14. Additionally, removal of the T-handle after proper positioning of the cannula/stylet combination 15 provides a less obstructed view of the operating corridor and surgical target site. As shown and described herein, the cannula 12 and stylet 14 are generally cylindrical in shape. However, it should be understood that cannula 12 and stylet 14 may be provided in any suitable shape having any suitable cross-section (e.g. generally oval or polygonal) without deviating from the scope of the present invention.

Figure 2:
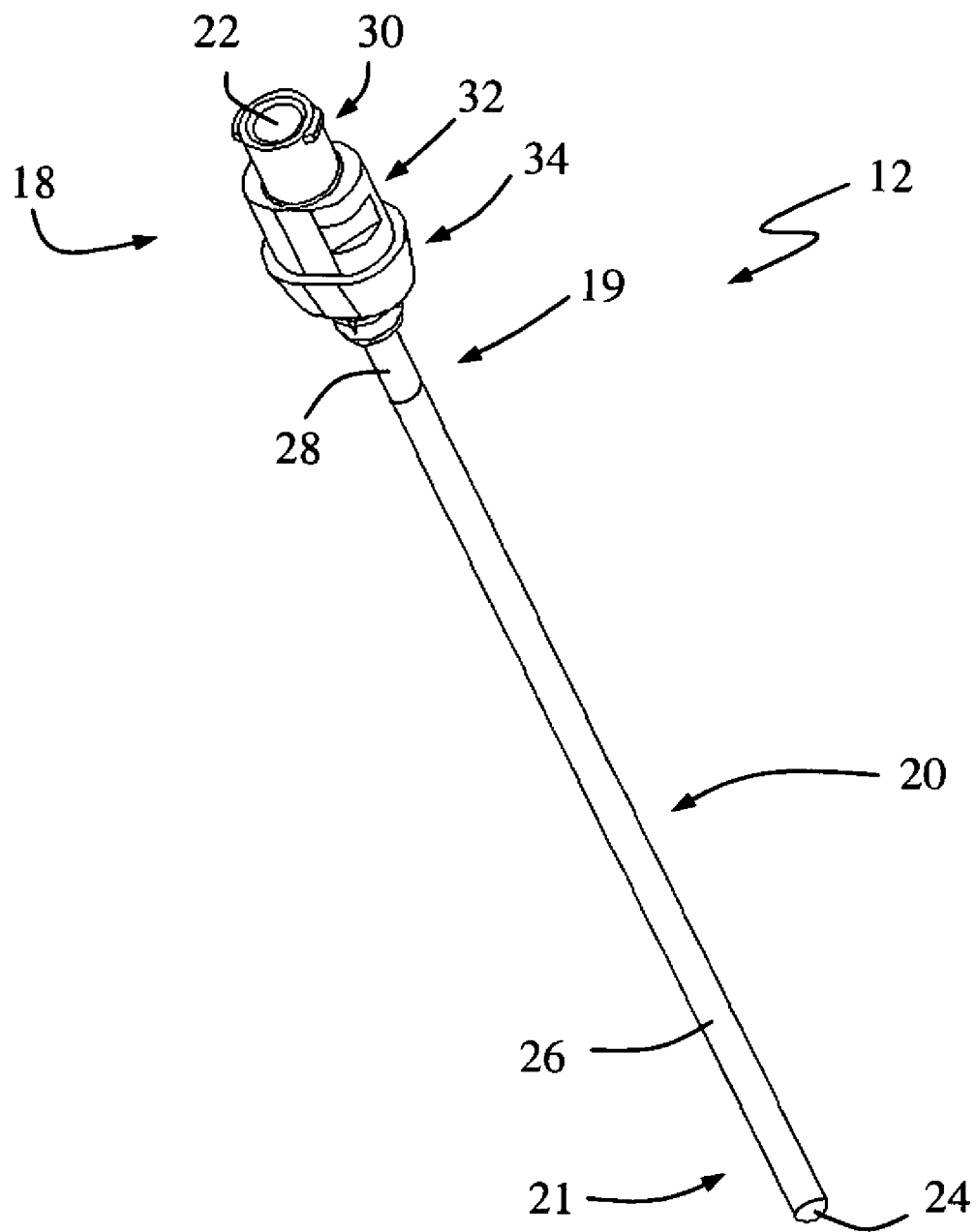
FIG. 2 is a perspective view of a cannula forming part of the pedicle access system of FIG. 1.

FIG. 2 illustrates an example of a cannula 12 forming part of pedicle access system 10. Cannula 12 includes a coupling element 18 and an elongated shaft 20. An interior lumen extends through the cannula 12 from a first opening 22 located at a proximal region 30 of the coupling element 18 to a second opening 24 located at a distal end 21 of the elongated shaft 20. Elongated shaft 20 may be composed of any conductive material such as (by way of example only) metal. A polymeric coating is provided on a substantial portion of the exterior surface of elongated shaft 20 such that elongated shaft 20 comprises an insulated portion 26 and an uninsulated portion 28. Although elongated shaft 20 is shown having a single uniform diameter, it will be appreciated that one or more diameter changes may be incorporated along the elongated shaft 20 without deviating from the scope of the present invention.

Figure 3:
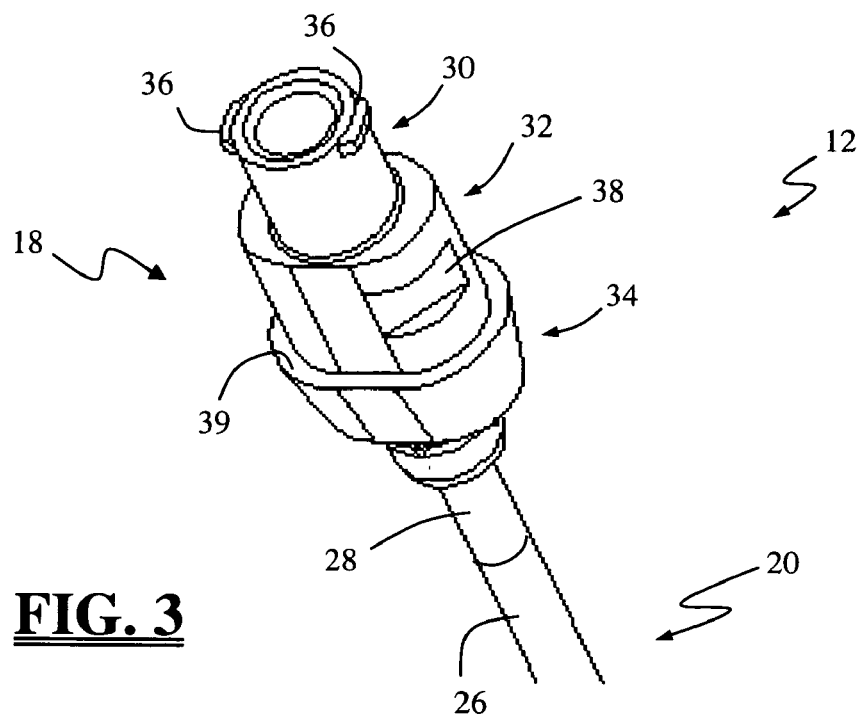
FIG. 3 is a perspective view of a coupling element forming part of the cannula of FIG. 2.

With reference to FIG. 3, coupling element 18 comprises a proximal region 30, a center section 32, and a base portion 34. Proximal region 30 is dimensioned to engage with the stylet 14 (described below). Proximal region 30 may include at least one tab member 36 that protrudes in a generally lateral direction from the proximal region 30. By way of example only, as shown in FIG. 3 proximal region 30 includes two tab members 36 positioned opposite one another and adjacent to first opening 22. As will be described in greater detail below, tab members 36 function to lock the cannula 12 and stylet 14 together. Center section 32 is dimensioned to be received within T-handle aperture 66 (FIG. 16) as described in further detail below. Center section 32 may be provided with at least one cutout 38 dimensioned to receive a locking mechanism 68 (FIG. 16) incorporated into T-handle 16 to secure the T-handle 16 to the cannula/stylet combination 15, or optionally to the cannula 12 only. The base 34 has a circumference that is greater than the circumference of center section 32, such that a ledge 39 is formed at the interface of center section 32 and the base portion 34. The ledge 39 engages the rim 72 of T-handle 16 so as to minimize potential stress on a T-handle locking mechanism 68 discussed below.

Figure 4:
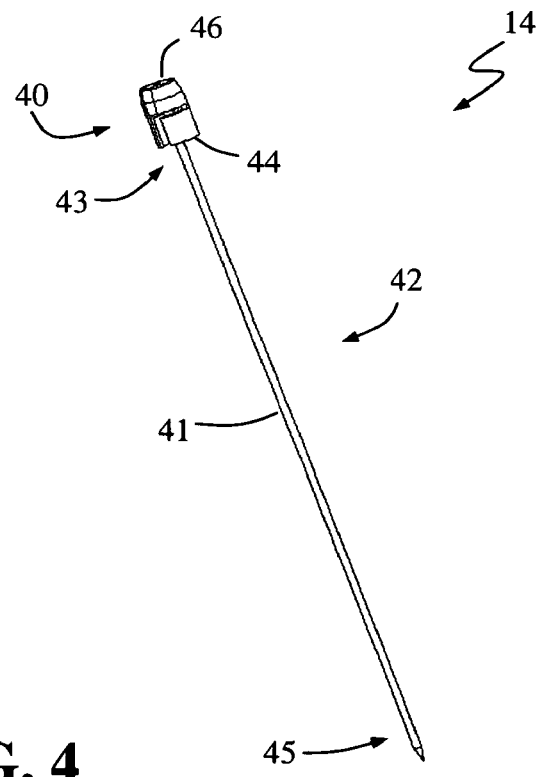
FIG. 4 is a perspective view of a stylet forming part of the pedicle access system of FIG. 1.
Figure 5:
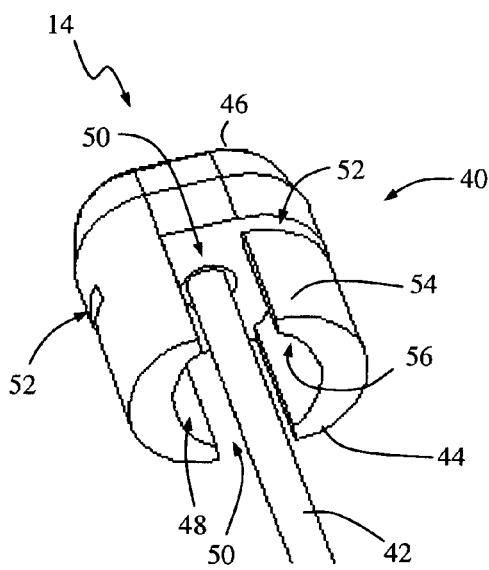
FIG. 5 is a perspective view of a locking cap forming part of the stylet of FIG. 4.

FIG. 4 illustrates an example of a stylet 14 forming part of the pedicle access system 10. Stylet 14 includes a locking cap 40 and a needle element 42. Locking cap 40 has a similar size and shape to center section 32, and is similarly dimensioned to be received within T-handle aperture 66, discussed below. Locking cap 40 includes a distal end 44 and a proximal end 46. As illustrated in FIG. 5, locking cap 40 includes a generally cylindrical aperture 48 having an opening at distal end 44 and extending in a proximal direction at least partially the length of locking cap 40. Generally cylindrical aperture 48 is dimensioned to receive the generally cylindrical proximal region 30 of cannula 12. Furthermore, locking cap 40 includes at least one longitudinal channel 50 (defined by an axis extending through the proximal and distal ends 46, 44 respectively) and at least one lateral channel 52 extending generally perpendicularly from longitudinal channel 50. Longitudinal channel 50 and lateral channel 52 each extend from an exterior surface 54 through an interior surface 56 into aperture 48. Preferably, the number of longitudinal channels 50 and lateral channels 52 correspond to the number of tab members 36 on cannula 12. By way of example only (and as shown in FIGS. 3-5), cannula 12 includes two tab members 36 and stylet 14 includes two longitudinal channels 50 and two lateral channels 52.

Figure 12:
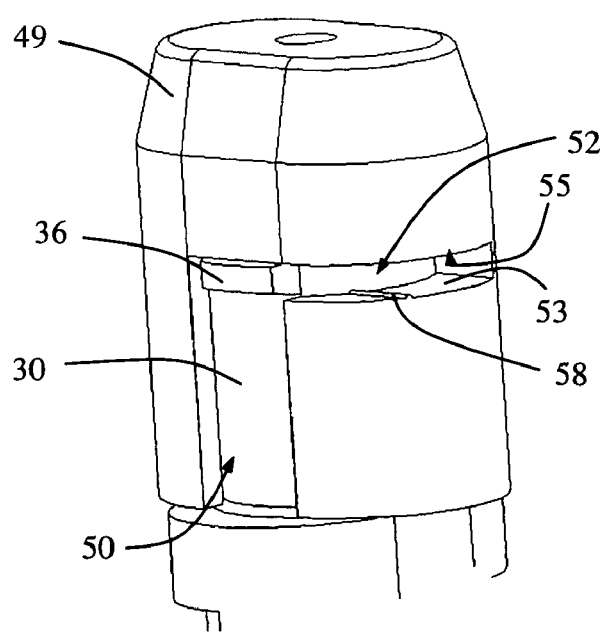
FIG. 12 is perspective view of the locking cap of the fully inserted stylet of FIG. 11, shown in an unlocked position.
Figure 13:
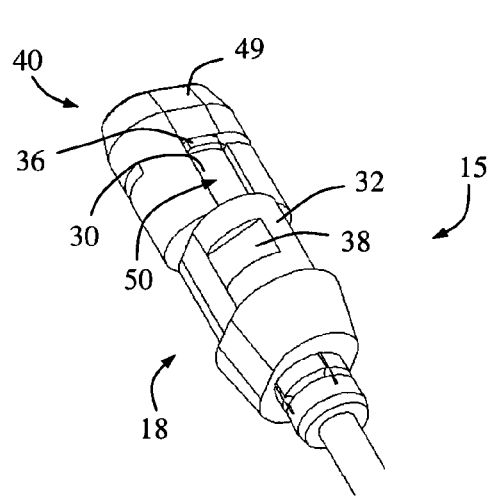
FIG. 13 is a perspective view of the cannula and stylet combination in the unlocked position of FIG. 11.

Longitudinal channel 50 initiates at the distal end 46 and has a length corresponding to the length of the generally cylindrical 48. Lateral channel 52 initiates at the proximal end of longitudinal channel 50 and extends generally perpendicularly therefrom such that together the longitudinal and lateral channels 50, 52 form a generally half-T shape. Longitudinal channel 50 and lateral channel 52 function to interact with the tab 36 on cannula 12, so as to lock the stylet 14 and cannula 12 together. Longitudinal channel 50 has a width dimension sufficient to accommodate the length of tab member 36 and lateral channel 52 has a height dimension sufficient to accommodate the height of tab member 36 (best viewed in FIG. 12). A ridge 58 (shown in FIG. 12) may be positioned along the distal-most edge 53 and/or proximal-most edge 55 of the lateral channel 52 to engage with tab member 36 and provide a locking means for the cannula/stylet combination 15. Additionally, a portion of exterior surface 54 adjacent to proximal end 46 may comprise a ramped surface 49 such that the circumference of distal end 44 is slightly greater than the circumference of proximal end 46, so as to facilitate engagement with the T-handle 16.

Figure 6:
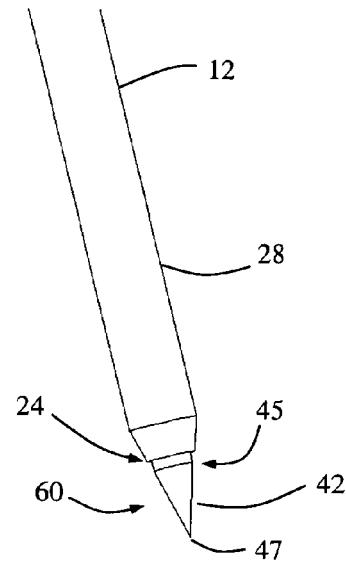
FIG. 6 is a perspective view of the distal portion of the stylet of FIG. 4 protruding from the distal region of the cannula of FIG. 2.

The needle element 42 comprises an elongated shaft 41 having a proximal region 43 and a distal region 45. The proximal region 43 may be attached to the interior of locking cap 40 between proximal end 46 and aperture 48. Elongated shaft 41 extends distally from proximal region 43 with a significant portion protruding generally perpendicularly from the opening of aperture 48. Needle element 42 is dimensioned to be inserted through the interior lumen of cannula 12. The distal region 45 generally includes a distal portion of elongated shaft 41 and a shaped tip 47 having any form or shape capable of being driven into the pedicle to create a pilot hole. By way of example only, shaped tip 47 may have a beveled or double diamond form. As illustrated in FIG. 6, when needle element 42 is fully inserted into cannula 12, at least a portion of distal region 45 (including shaped tip 47) may protrude slightly from the second opening 24 of cannula 12. Due to the insulated nature of cannula 12, the portion of needle element 42 that protrudes from cannula 12 effectively constitutes a stimulation region 60. The stimulation region 60 may include the distal region 45 and/or the shaped tip 47.

Figure 7:
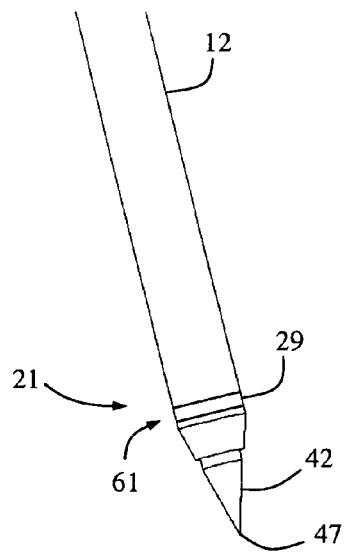
FIG. 7 is a perspective view of the distal portion of the stylet of FIG. 4 protruding from the distal region of the cannula of FIG. 2, with the distal region of the cannula having an non-insulated portion.
Figure 8:
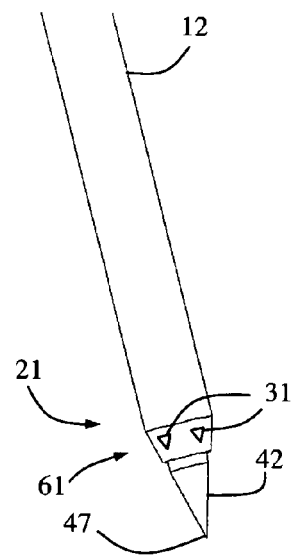
FIG. 8 is a perspective view of the distal portion of the stylet of FIG. 4 protruding from the distal region of the cannula of FIG. 2, with the distal region of the cannula having a directional electrode.

According to a further aspect of the present invention, any part of the needle element 42 (e.g. the elongated shaft 41, distal region 45 and/or shaped tip 47) may be provided with a coating to insulate and therefore limit or reduce the stimulation region 60 to a desired configuration. For example, the distal tip 47 may have an insulation coating to effectuate a stimulation region 60 consisting of the portion of the distal region 45 of the needle element 42 between the insulated cannula 12 and the insulated distal tip 47. Alternatively, the entirety of needle element 42 may be provided with an insulative coating and the distal region 21 of cannula 12 may be provided with (for example) one or more non-insulated portions 29 (FIG. 7) and/or one or more directional electrodes 31 (FIG. 8) forming a stimulation region 61. These alternative arrangements serve to mitigate an apparent phenomenon in which certain geometries (e.g. points and edges) tend to generate significantly higher current densities and therefore are much more efficient at exciting a nearby nerve, even through bone tissue.

Needle element 42 may be composed of a conductive material, such as metal. Alternatively, needle element 42 may be composed of a non-conductive material with one or more embedded conductive elements at or near the distal end (e.g. distal region 45 and/or shaped tip 47) capable of being communicatively linked with a pedicle integrity testing system.

Figure 9:
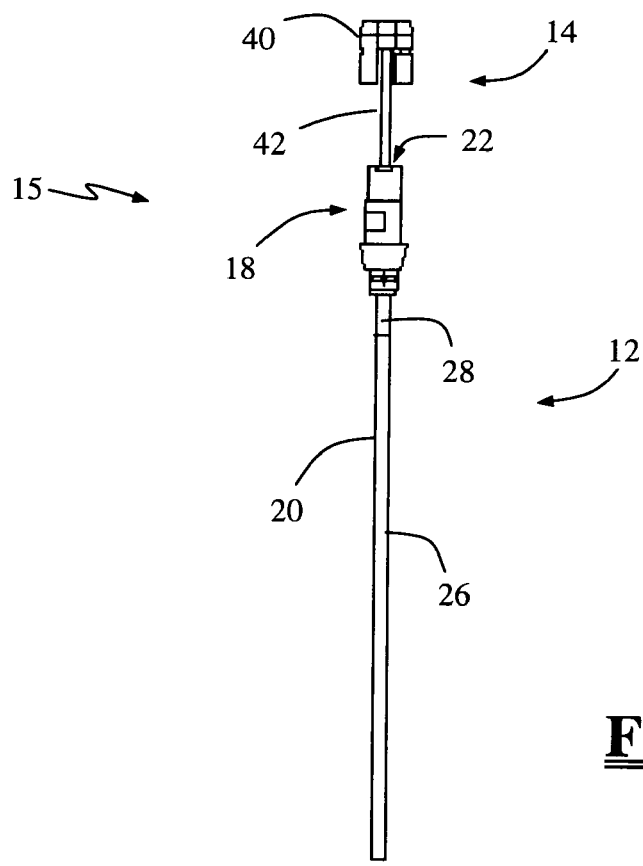
FIGS. 9-10 are plan and perspective views, respectively, of the stylet of FIG. 4 partially inserted into the cannula of FIG. 2.
Figure 10:
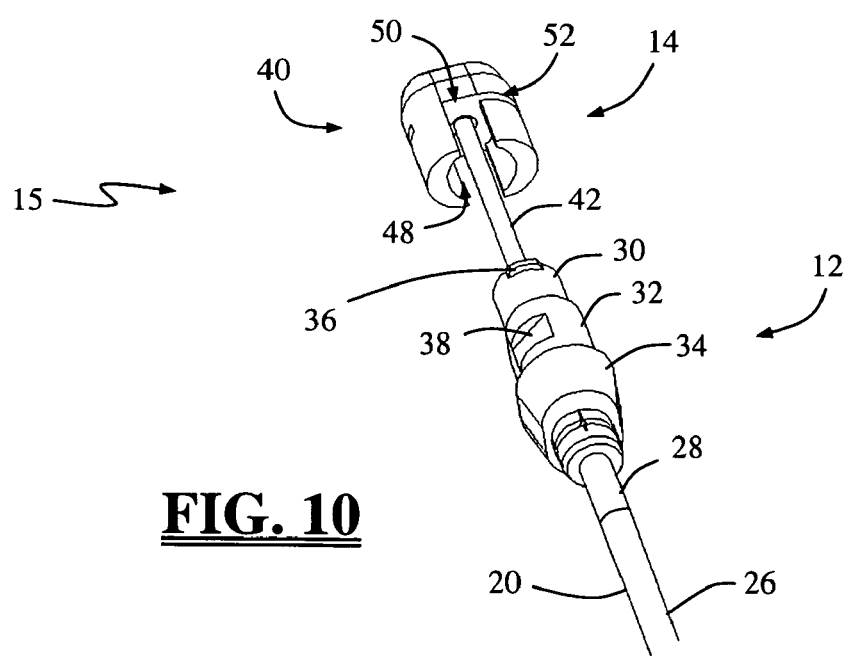
Figure 11:
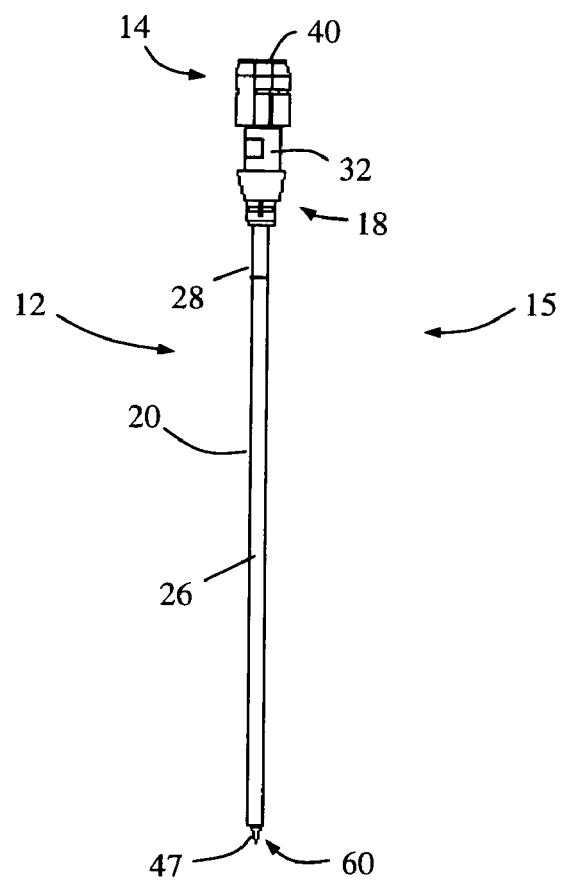
FIG. 11 is a is a plan view of the stylet of FIG. 4 fully inserted into the cannula of FIG. 2 in an unlocked position.
Figure 14:
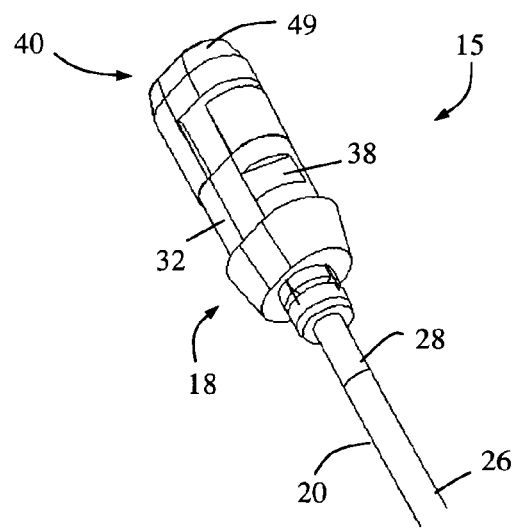
FIGS. 14-15 are perspective and plan views, respectively, of the cannula and stylet combination of FIG. 13 in the locked position.
Figure 15:
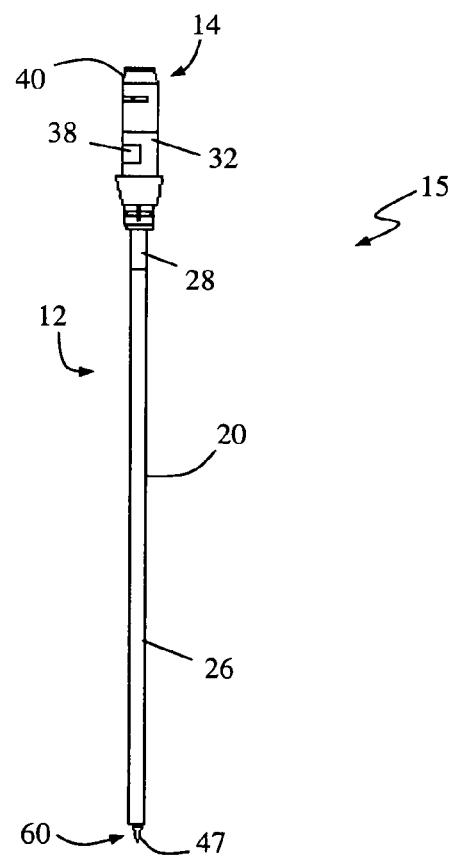

FIGS. 9-15 illustrate the formation of the cannula/stylet combination 15. In FIGS. 9-10 stylet 14 is introduced into cannula 12. Needle element 42 of stylet 14 is inserted into the interior lumen of cannula 12 through the first opening 22 of coupling element 18. The locking cap 40 of stylet 14 is positioned such that its longitudinal channels 50 are aligned with the tab members 36 of cannula 12. The proximal region 30 of cannula 12 is received into the aperture 48 of locking cap 40, and the tab members 36 pass through the longitudinal channels 50 as insertion of needle element 42 progresses. Insertion is complete when the proximal portion 30 is fully received by aperture 48, leaving the locking cap 40 in the "unlocked" position illustrated in FIGS. 11-13. As mentioned above, the distal region 45 of needle element 42 including shaped tip 47 (and the stimulation region 60) may protrude from the second opening 24 of the elongated shaft 20 of cannula 12 when stylet 14 is fully inserted, shown in FIG. 11. In the unlocked position, tab members 36 are positioned at the proximal end of longitudinal channels 50 where the channels intersect lateral channels 52. At this point, the corresponding shapes of the locking cap 40 of stylet 14 and center section 32 of cannula 12 are out of alignment. To lock stylet 14 in place and complete the combination, the locking cap 40 is rotated until it is aligned with the center section 32 as illustrated in FIGS. 14-15. As the lateral channels 52 rotate around the tab members 36, ridges 58 come into contact with the tab members 36. The ridges may not pass the tab members 36 if the locking cap 40 is not rotated with enough force to deform the ridges 58. Once the ridges 58 have deformed, the rotation may continue towards the final position. The locking cap 40 and center section 32 become aligned and the ridges 58 may clear the tab members 36 and regain their original forms, thereby preventing inadvertent rotation of the locking cap 40 back to the unlocked position.

Figure 16:
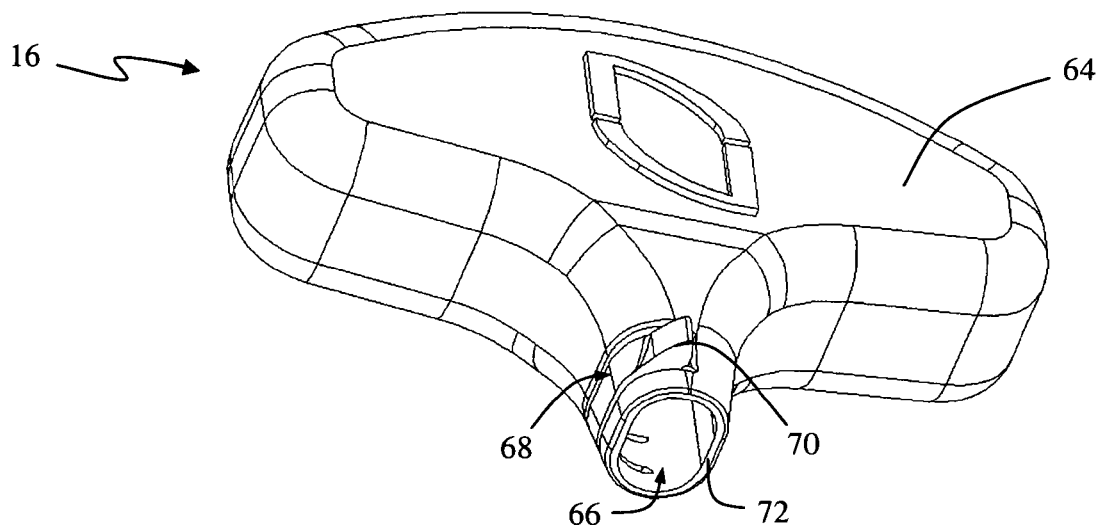
FIGS. 16-17 are perspective views of a T-handle forming part of the pedicle access system of FIG. 1.
Figure 17:
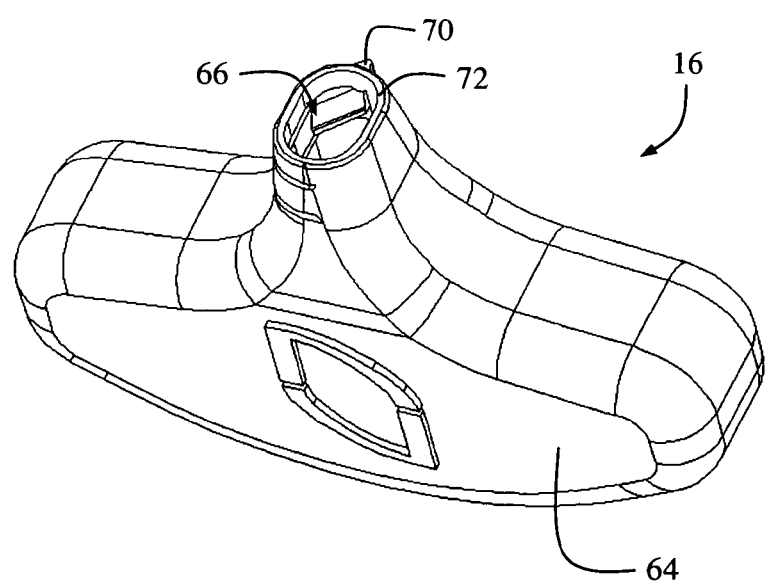
Figure 18:
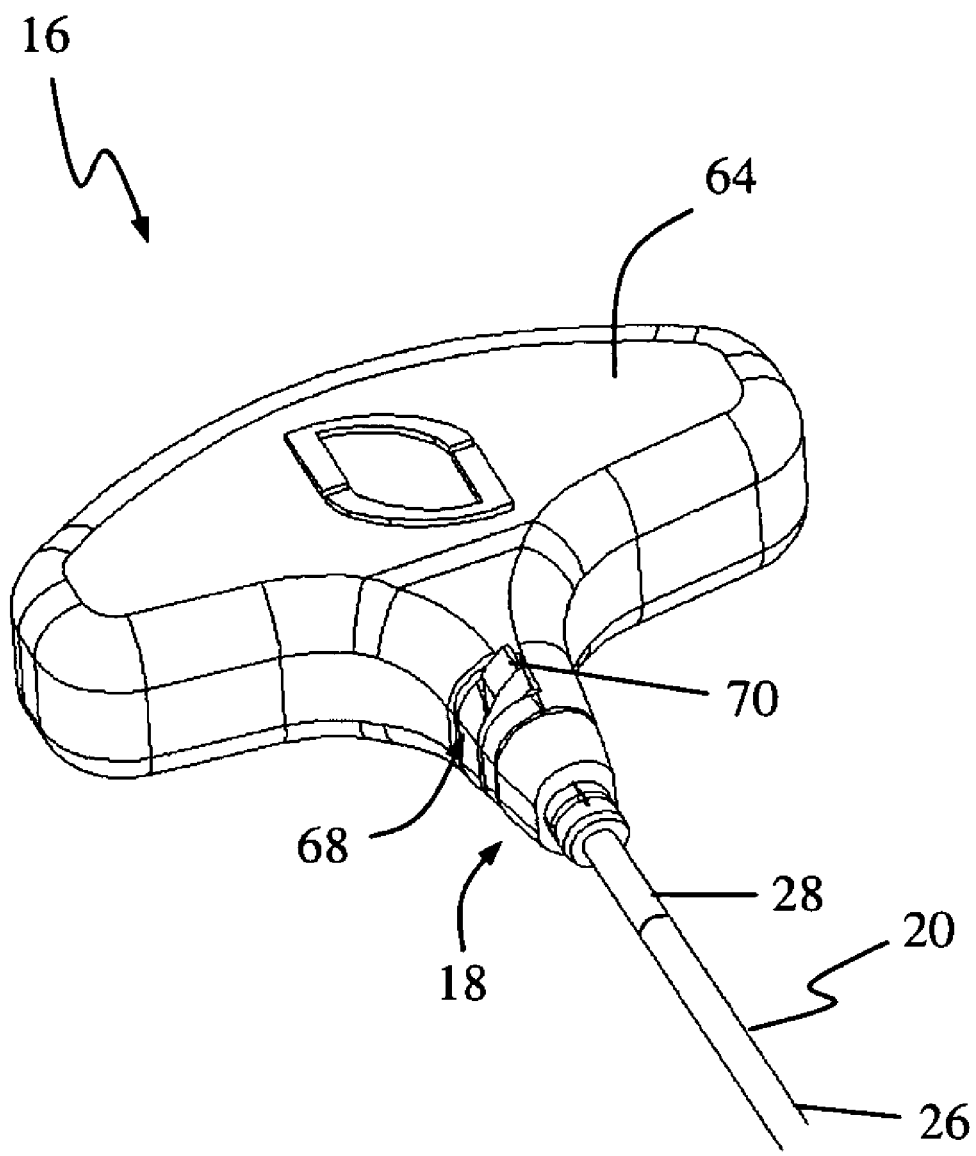
FIG. 18 is a perspective view of the pedicle access system of FIG. 1 with the cannula and stylet combination of FIG. 13 fully inserted and locked in the T-handle.

FIG. 16 illustrates an example of a T-handle 16 forming part of the pedicle access system 10. T-handle 16 includes a grip region 64, an aperture 66 for engaging the cannula 12 or cannula/stylet combination 15, and a locking mechanism 68 for securing the T-handle to the cannula 12. Grip region 64 may be provided in any number of suitable shapes and sizes that may aid the user in holding and manipulating the pedicle access system 10 during use. The T-handle aperture 66 is dimensioned to snugly receive both the locking cap 40 and center section 32 when they are aligned in the locked position as described above. The locking mechanism 68 preferably comprises a lever having one end that is integrated into the aperture wall and a free end 70 extending therefrom. The majority of the locking mechanism 68 (excluding free end 70) may comprise the same thickness as the aperture wall and does not protrude, interiorly or exteriorly, from the aperture wall. In its "natural" state, the interior surface of free end 70 protrudes into the aperture 66 space. The interior surface of free end 70 is dimensioned to engage the cutout 38 in the center section 32 of cannula 12. Furthermore, as illustrated in FIG. 17, the interior surface of free end 70 may be slightly ramped, such that the edge further from the aperture opening protrudes further into the aperture than the edge closer to the aperture opening. The ramped portion works in concert with the ramped surface 49 at the proximal end 46 of locking cap 40 to force the free end 70 out of its natural state as the locking cap 40 of stylet 14 and center section 32 of cannula 12 are received into the T-handle aperture 66. When the locking cap 40 and center section 32 are fully inserted into the T-handle aperture 66, as illustrated in FIG. 18, the interior surface of free end 70 aligns with the cutout 38 in the center section 32 and free end 70 returns to its natural state, thus locking the T-handle 16 to the cannula 12. Furthermore, as the locking cap 40 and center section 32 are fully inserted into the T-handle aperture 66, the ledge 39 engages the rim 72. This interaction functions to minimize potential stress on the T-handle locking mechanism 68 by increasing the surface area that receives force applied by the user. To remove the T-handle 16, the free end 70 may be lifted to disengage with the cutout 38, and the T-handle may be pulled off. Optionally, T-handle 16 may be cannulated (not shown) such that an interior lumen extends from an opening on the top of the handle into the aperture 66.

Figure 19:
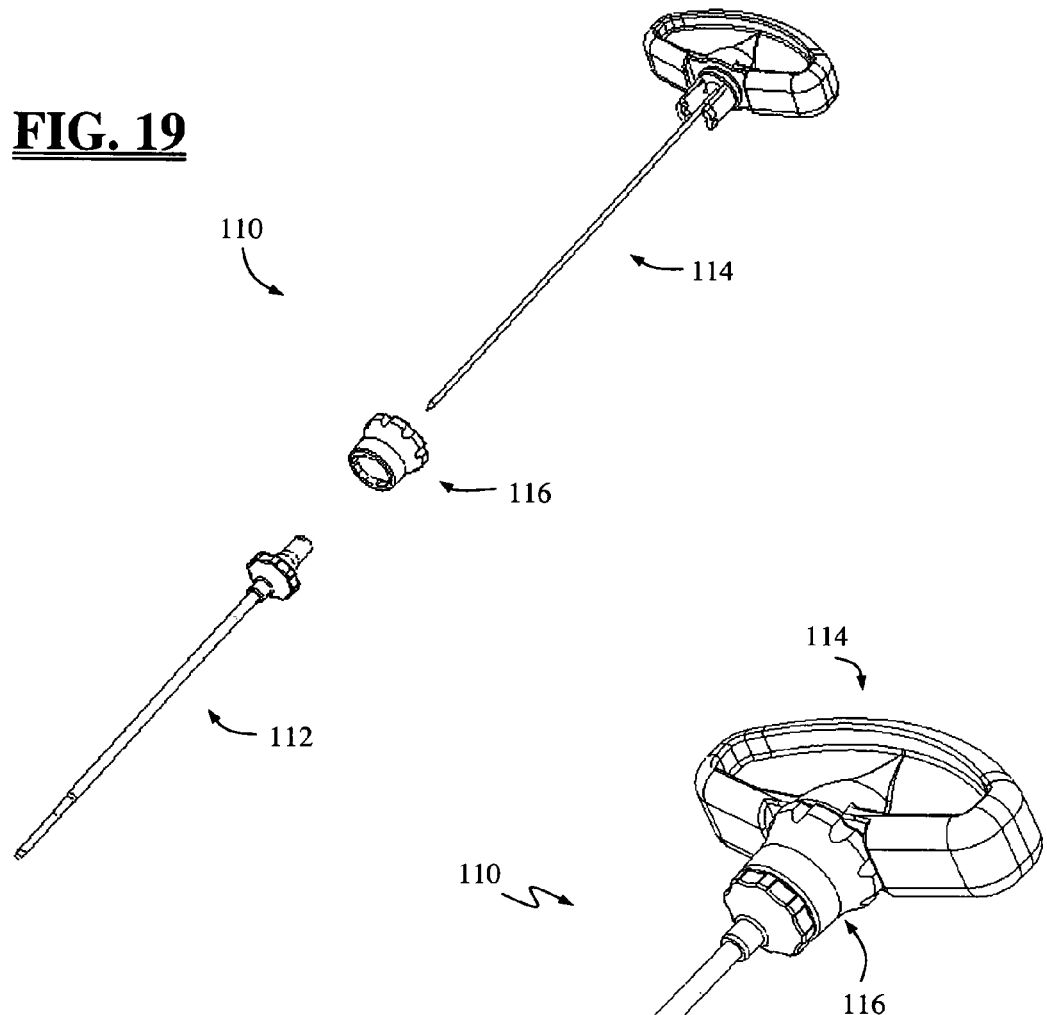
FIG. 19 is an exploded perspective view of a pedicle access system according to an alternative embodiment of the present invention.
Figure 20:
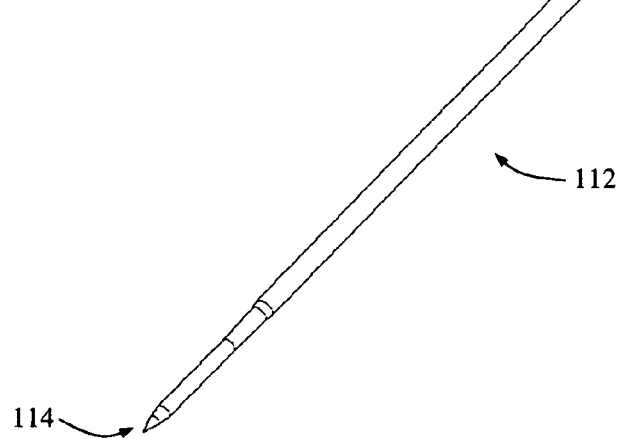
FIG. 20 is a perspective view of the assembled pedicle access system of FIG. 19.

FIGS. 19-20 illustrate an example of a pedicle access system 110 according to an alternative embodiment of the present invention. The pedicle access system 110 includes a cannula 112, a stylet 114, and a lock collar 116. As described above in relation to pedicle access system 10, pedicle access system 110 may be used to percutaneously approach the pedicle, initiate pilot hole formation, and conduct a stimulation signal to the target site for the purposes of performing a pedicle integrity assessment during formation of the pilot hole. To do this, the cannula 112 and stylet 114 may be lockingly mated and inserted through an operating corridor to the pedicle target site, using the handle portion 140 of the stylet 114 to facilitate easy movement and positioning of pedicle access system 110. The pedicle access system 110 may be driven into the bone at the target site to form a pilot hole while a stimulation signal is applied and conducted to the target site to assess the integrity of the pedicle during hole formation. As shown and described herein, the cannula 112 and stylet 114 are generally cylindrical in shape. However, it should be understood that cannula 112 and stylet 114 may be provided in any suitable shape having any suitable cross-section (e.g. generally oval or polygonal) without deviating from the scope of the present invention.

Figure 21:
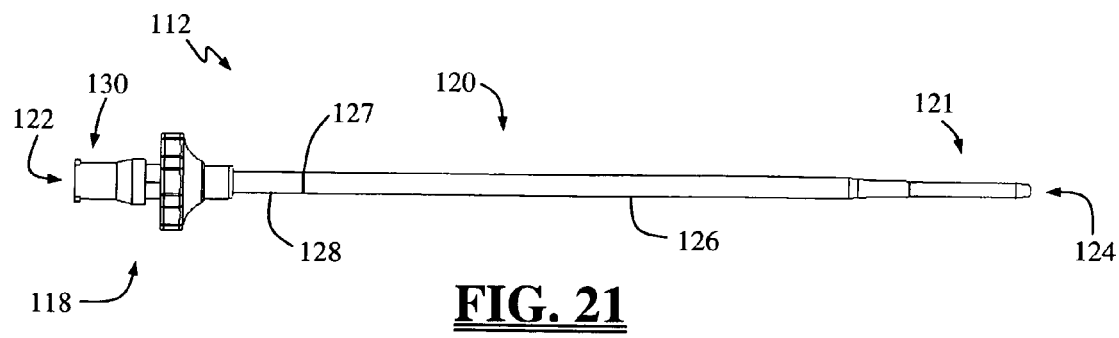
FIGS. 21-22 are plan and perspective views, respectively, of a cannula forming part of the pedicle access system of FIG. 20.
Figure 22:
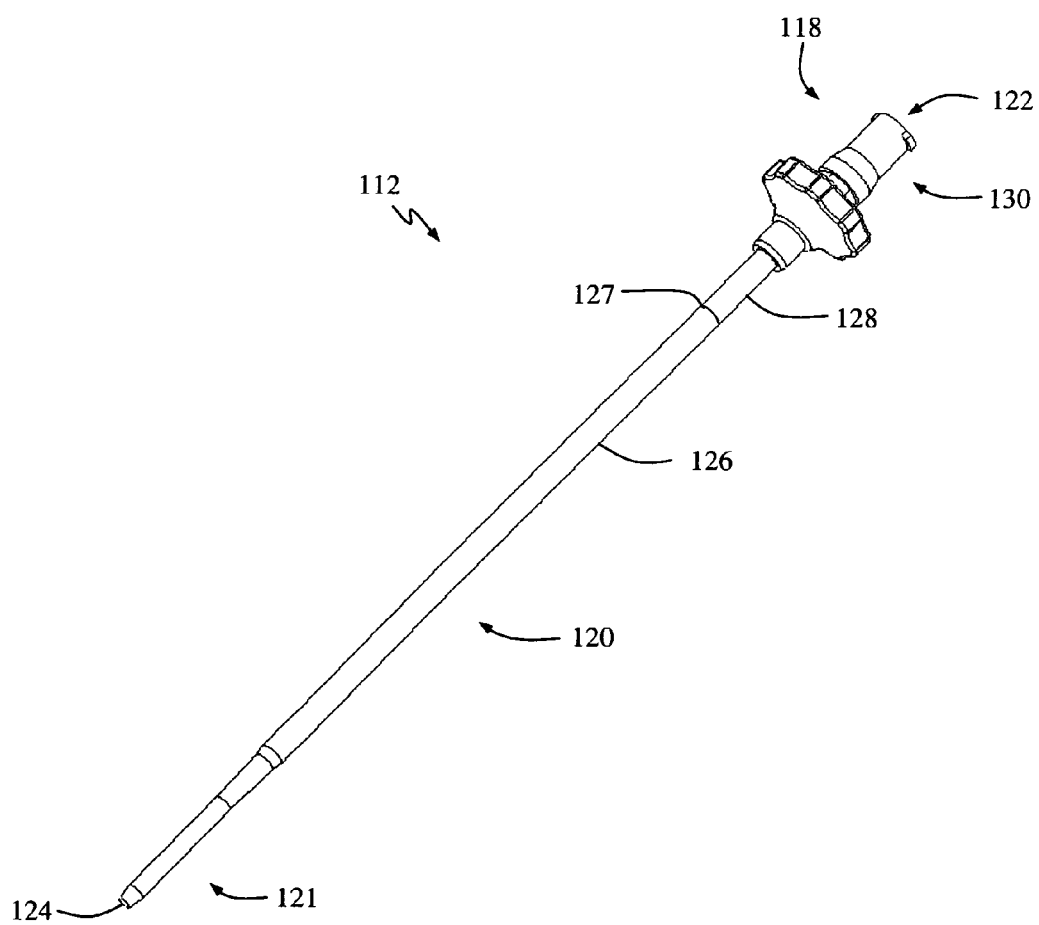

FIGS. 21-22 illustrate an example of a cannula 112 forming part of pedicle access system 110. Cannula 112 includes a coupling element 118 and an elongated shaft 120. An interior lumen extends through the cannula 112 from a first opening 122 located at a proximal region 130 of the coupling element 118 to a second opening 124 located at a distal end 121 of the elongated shaft 120. Elongated shaft 120 may be composed of any conductive material such as metal, for example. A polymeric coating may be provided on a substantial portion of the exterior surface of elongated shaft 120 such that elongated shaft 120 comprises an insulated portion 126 and an non-insulated portion 128 (the edge of the coating and thus the boundary between portions 126, 128 represented by callout 127 in FIGS. 21-22). Elongated shaft 120 may include any number of diameter changes incorporated along its length without deviating from the scope of the present invention. In the alternative, elongated shaft 120 may be provided with a uniform diameter along its length.

Figure 23:
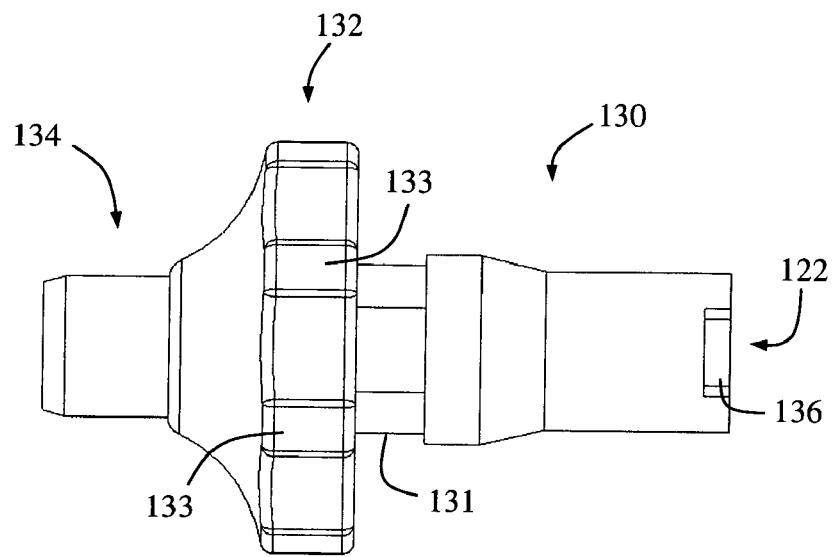
FIGS. 23-24 are plan and perspective views, respectively, of a coupling element forming part of the cannula of FIG. 21.
Figure 24:
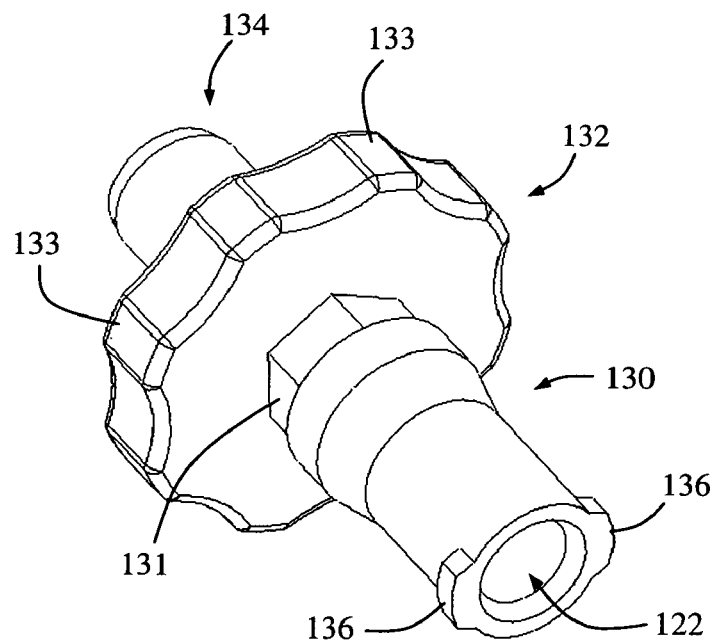

With reference to FIGS. 23-24, coupling element 118 comprises a proximal region 130, a center section 132, and a distal portion 134. Proximal region 130 includes an engagement region 131 dimensioned to engage with the handle portion 140 of the stylet 114 (as described in further detail below). The engagement region 121 may be provided in any suitable geometric configuration to allow for secure mating with the engagement tabs 144 of the handle 140. By way of example only, the coupling element 118 is shown in FIGS. 23-24 having a hexagonal engagement region 131, however other shapes are possible. Proximal region 130 may include at least one tab member 136 that protrudes in a generally lateral direction from the proximal region 130. By way of example only, as shown in FIG. 24 proximal region 130 includes two tab members 136 positioned opposite one another and adjacent to first opening 122. Tab members 136 may be utilized to attach supplemental instruments and/or apparatuses to the cannula 112. Center section 132 may be provided with a diameter that is larger than the diameters of the proximal region 130 and distal portion 134, and may be provided with a plurality of ridges 133 and/or other features for the purpose of providing a suitable gripping area for a user. The distal portion 134 is dimensioned to engage with the elongated shaft 120 of the cannula 112.

Figure 25:
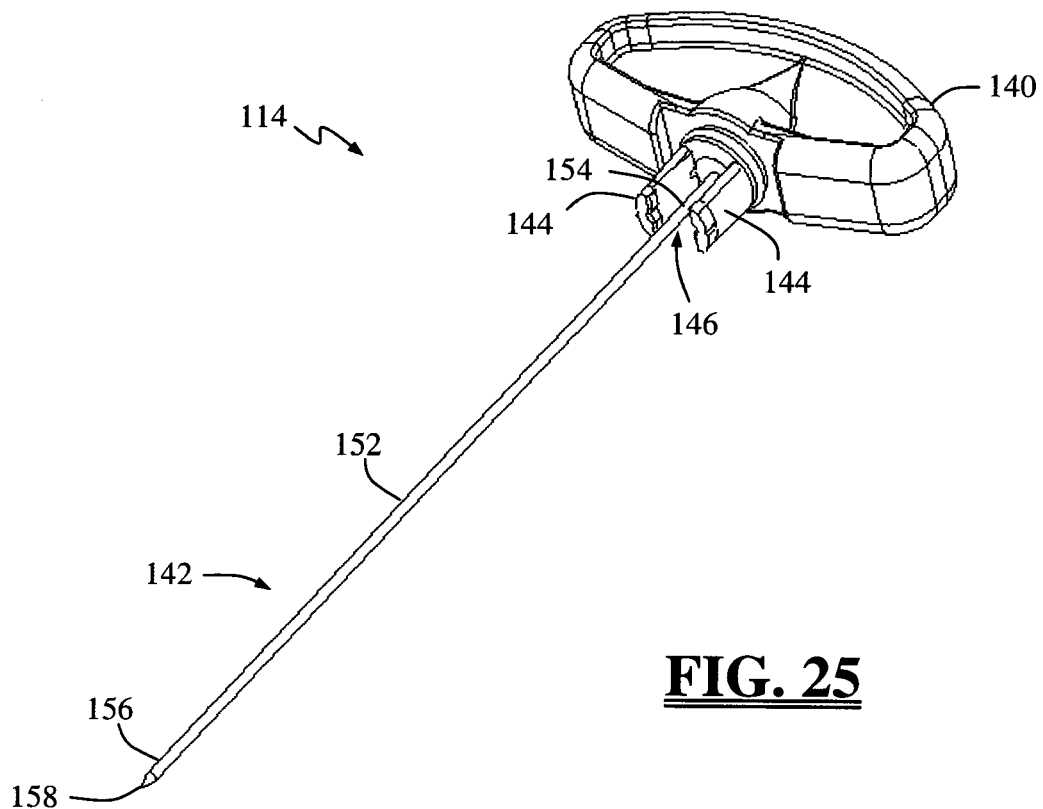
FIG. 25 is a perspective view of a stylet forming part of the pedicle access system of FIG. 20.
Figure 26:
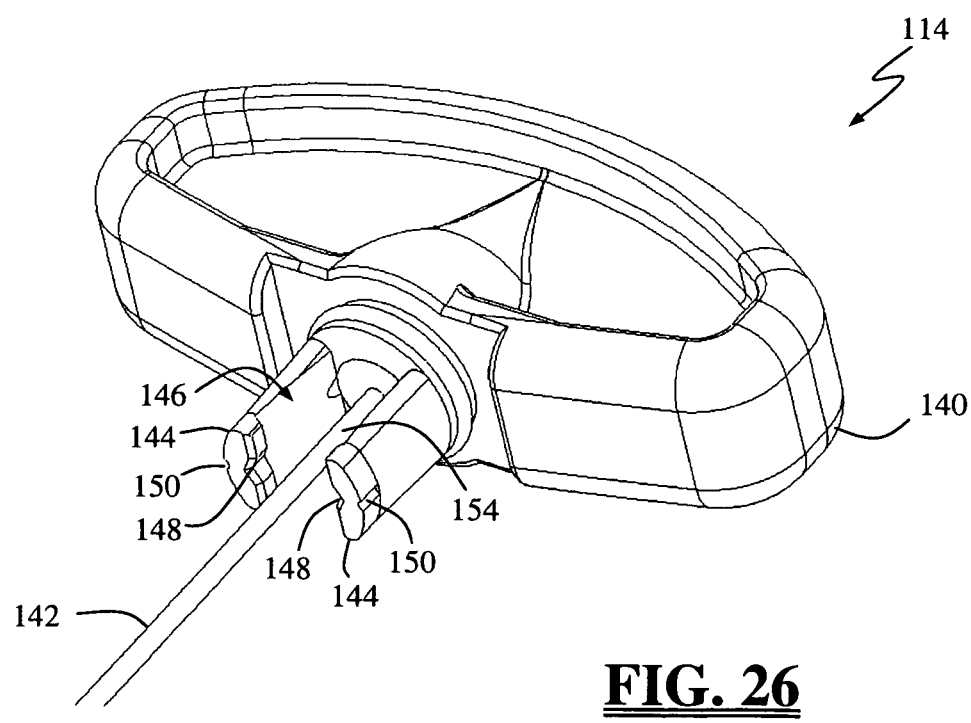
FIG. 26 is a perspective view of a handle forming part of the stylet of FIG. 25.

FIG. 25 illustrates an example of a stylet 114 forming part of the pedicle access system 110. Stylet 114 includes a handle portion 140 and a needle element 142. Handle portion 140 may (by way of example) resemble a T-handle for providing a user with a suitable gripping means. Handle portion 140 may be provided with a pair of engagement tabs 144 extending distally from handle portion 140. Engagement tabs 144 extend generally perpendicularly from the handle 140 and generally parallel to one another such that the engagement tabs 144 collectively form an interior space 146. Interior space 146 is dimensioned to receive the proximal region 130 of the coupling element 118 of the cannula 112. Each engagement tab 144 is provided with a medial (inwardly-facing) indentation 148 and a lateral (outwardly-facing) indentation 150. Medial indentations 148 are dimensioned to engage the engagement region 131 of the coupling element 118, described above. For this reason, the medial indentations 148 may be provided with any geometry complementary to the shape of the engagement region 131 such that when mated, the engagement tabs 144 (via the medial indentations 148) will prevent movement of the engagement region 131, in effect locking the cannula 112 in place relative to the stylet 114. The lateral indentations 150 are dimensioned to interact with the first and second protrusions 170, 172 of the lock collar 116 described in further detail below.

Figure 27:
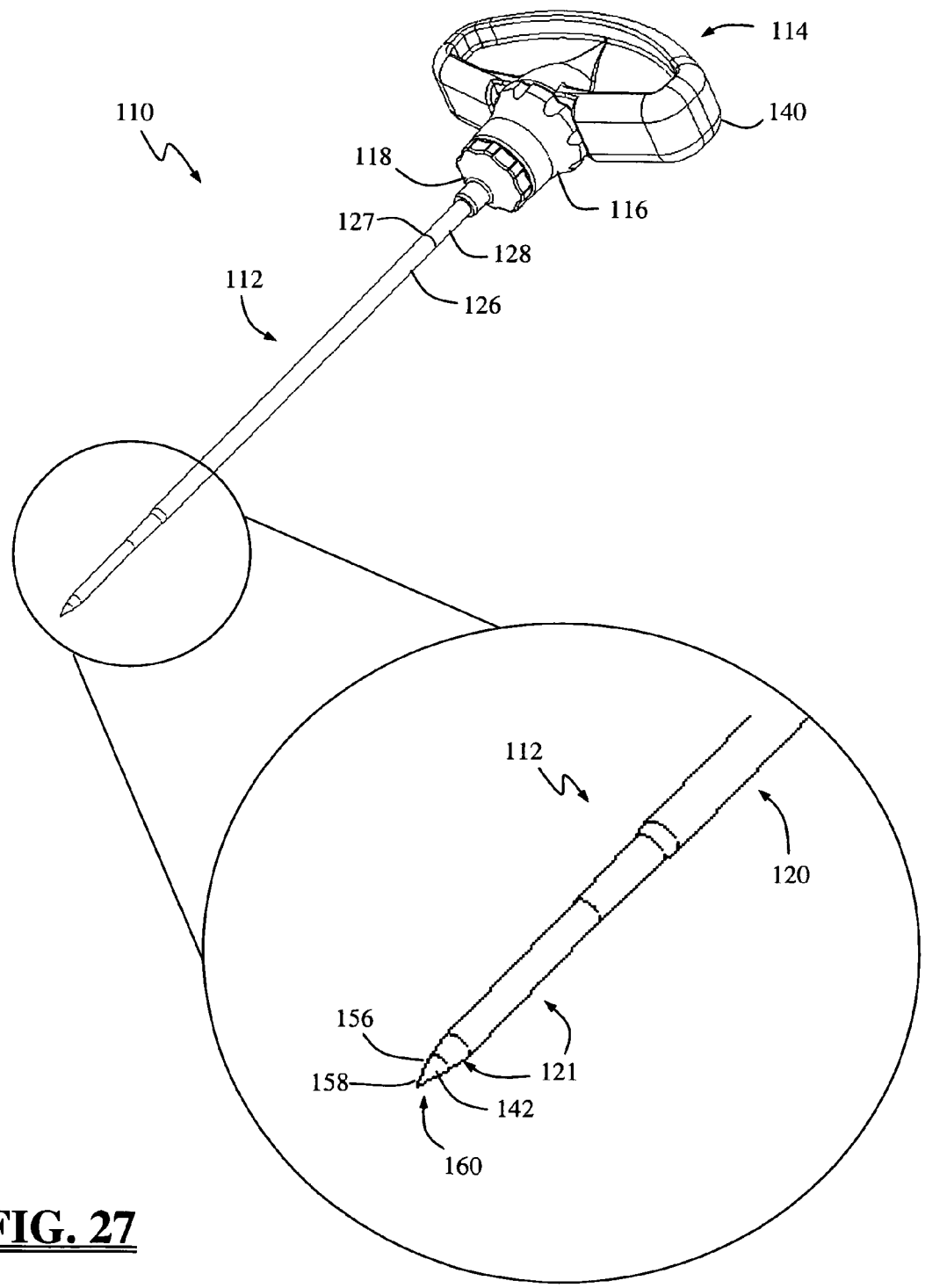
FIG. 27 is a perspective view of the pedicle access system of FIG. 20 including an enlarged view of a distal region thereof.
Figure 31:
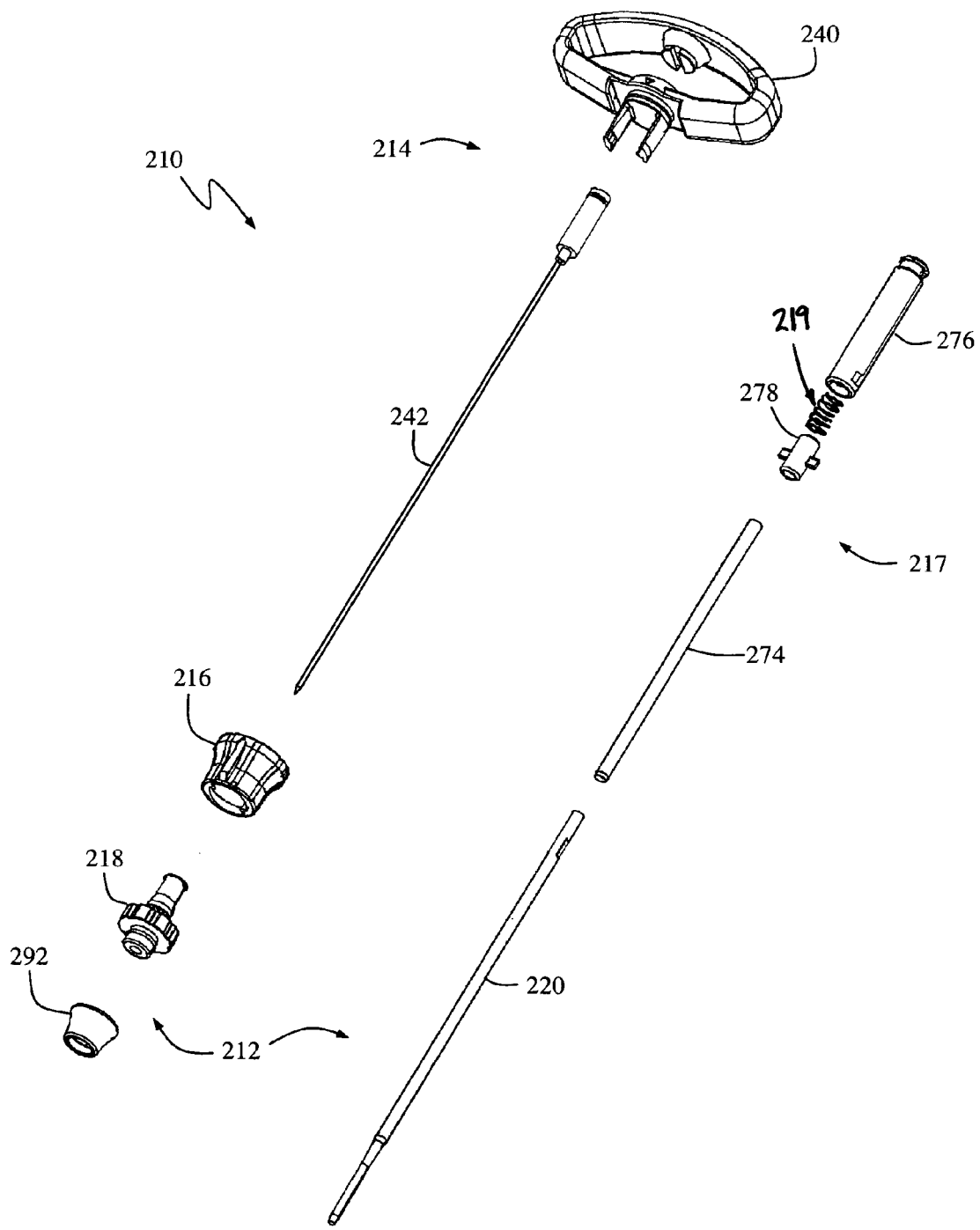
FIG. 31 is an exploded perspective view of a pedicle access system according to a further alternative embodiment of the present invention.

The needle element 142 comprises an elongated shaft 152 having a proximal region 154 and a distal region 156. The proximal region 154 may be attached to the interior of handle portion 140. Elongated shaft 152 extends distally from proximal region 154 and generally perpendicularly from the handle 140. Needle element 142 is dimensioned to be inserted through the interior lumen of cannula 112. The distal region 156 generally includes a distal portion of elongated shaft 152 and a shaped tip 158 having any form or shape capable of being driven into the pedicle to create a pilot hole. By way of example only, shaped tip 158 may have a beveled or double diamond form. As illustrated in FIG. 27, when needle element 142 is fully inserted into cannula 112, at least a portion of distal region 156 (including shaped tip 158) may protrude slightly from the second opening 124 of cannula 112. Due to the insulated nature of cannula 112, the portion of needle element 142 that protrudes from cannula 112 effectively constitutes a stimulation region 160. The stimulation region 160 may include the distal region 152 and/or the shaped tip 158.

According to a further aspect of the present invention, any part of the needle element 142 (e.g. the elongated shaft 152, distal region 156 and/or shaped tip 158) may be provided with a coating to insulate and therefore limit or reduce the stimulation region 160 to a desired configuration. For example, the distal tip 158 may have an insulation coating to effectuate a stimulation region 160 consisting of the portion of the distal region 156 of the needle element 142 between the insulated cannula 112 and the insulated distal tip 158. This coating serves to mitigate an apparent phenomenon in which certain geometries (e.g. points and edges) tend to generate significantly higher current densities and therefore are much more efficient at exciting a nearby nerve, even through bone tissue.

Needle element 142 may be composed of any conductive material, such as metal. Alternatively, needle element 142 may be composed of a non-conductive material with one or more embedded conductive elements at or near the distal end (e.g. distal region 156 and/or shaped tip 158) capable of being communicatively linked with a pedicle integrity testing system.

With reference to FIGS. 28-30, a lock collar 116 is provided to lockingly mate the cannula 112 and the stylet 114. Lock collar 116 has a generally cylindrical overall shape, and includes a proximal portion 162, a distal portion 164 and an interior lumen 166 extending therethrough. The proximal portion 162 may have a diameter greater than that of the distal portion 164 and is provided with a plurality of friction elements 168 to allow a user to grasp and turn the lock collar 116. The distal portion 164 includes a generally oval-shaped opening 170 providing access to the lumen 166. The opening 170 further includes a pair of opposing first protrusions 172 and a pair of opposing second protrusions 174 located along the inside edge of opening 170. First protrusions 172 are located 180° from one another and are positioned at the long ends of the oval-shaped opening 170. Second protrusions 174 are positioned at the narrow sides of the oval-shaped opening 170 (and thus are located at 90° intervals from the first protrusions 172 and 180° from one another). First and second protrusions 172, 174 are each dimensioned to engage the lateral indentations 150 provided on the engagement tabs 144 of the handle 140, described above.

The interior lumen 166 is dimensioned to receive both of the engagement tabs 144 of the handle 140. Initially, the pedicle access system 110 of the present invention may be provided with the locking collar 116 attached to the stylet 114 in an initial position. This initial position is defined by the first protrusions 172 resting in the lateral indentations 150 of the engagement tabs 144 of the handle 140. Upon insertion of the needle element 142 into the cannula 112, the distal region 130 of the coupling element 118 of cannula 112 will enter the space 146 of the handle 140 such that the medial indentations 148 are aligned with (but not yet engaging) the engagement region 131 of the coupling element 118. At this point, a user would then rotate the lock collar 116 90° to a second position such that the second protrusions 174 rest in the lateral indentations 150. Due to the oval-shaped nature of the opening 170, upon rotation of the lock collar 116, the engagement tabs 144 will be forced toward one another, and the medial indentations 148 will come in contact with and positively engage the engagement region 131. As noted previously, this positive engagement prevents the cannula 112 from moving. At the same time, the lock collar 116 serves to lock the engagement tabs 114 in place, effectively locking the cannula 112 and the stylet 114 together. The pedicle access system 110 is now ready for use.

FIGS. 31-34 illustrate an example of a pedicle access system 210 according to a further alternative embodiment of the present invention. The pedicle access system 210 includes a cannula 212, a stylet 214, a lock collar 216 and a retractable insulation sheath 217. As described above in relation to pedicle access systems 10 and 110, pedicle access system 210 may be used to percutaneously approach the pedicle, initiate pilot hole formation, and conduct a stimulation signal to the target site for the purposes of performing a pedicle integrity assessment during formation of the pilot hole. To do this, the cannula 212 and stylet 214 may be lockingly mated and inserted through an operating corridor to the pedicle target site, using the handle portion 240 of the stylet 214 to facilitate easy movement and positioning of pedicle access system 210. The pedicle access system 210 may be driven into the bone at the target site to form a pilot hole while a stimulation signal is applied and conducted to the target site to assess the integrity of the pedicle during pilot hole formation. The retractable insulation sheath 217 functions to ensure maximum efficiency of the stimulation signal as by limiting or preventing shunting of the signal during pilot hole formation. As shown and described herein, the cannula 212, stylet 214 and retractable insulation sheath 217 are generally cylindrical in shape. However, it should be understood that cannula 212, stylet 214 and sheath 217 may be provided in any suitable shape having any suitable cross-section (e.g. generally oval or polygonal) without deviating from the scope of the present invention.

The retractable insulation sheath 217 functions to ensure maximum efficiency of the stimulation signal as by limiting or preventing shunting of the signal during pilot hole formation. With specific reference to FIGS. 32-34, this is accomplished by providing a tubular insulation member 274 slidably mated with a housing member 276 described in greater detail below. In an initial position (shown in FIGS. 33-34), the tubular insulation member 274 is fully extended such that it extends at least to the tip 258 of the stylet 214. Upon formation of a pilot hole in a pedicle (or other piece of bone), the stylet 214 will advance into the bone while the insulation sheath remains outside the bone (a position shown by way of example in FIG. 32). Due to the insulative properties of the sheath 217, the electrical current when supplied will be directed into the pilot hole by the non-insulated portion of the cannula 212 and stylet 214 while prevented from shunting outside of the hole by the sheath 217. This has the effect of reducing the current density of the applied stimulation signal as the exposed surface area of the non-insulated portion of the cannula 212 and the stylet 214 increases during introduction.

FIGS. 35-36 illustrate an example of a cannula 212 forming part of pedicle access system 210 of the present invention. Cannula 212 includes a coupling element 218 and an elongated shaft 220. An interior lumen extends through the cannula 212 from a first opening 222 located at a proximal region 230 of the coupling element 218 to a second opening 224 located at a distal end 221 of the elongated shaft 220. Elongated shaft 220 may be composed of any conductive material such as metal, for example. Elongated shaft 220 may include any number of diameter changes incorporated along its length without deviating from the scope of the present invention. In the alternative, elongated shaft 220 may be provided with a uniform diameter along its length.

Figure 37:
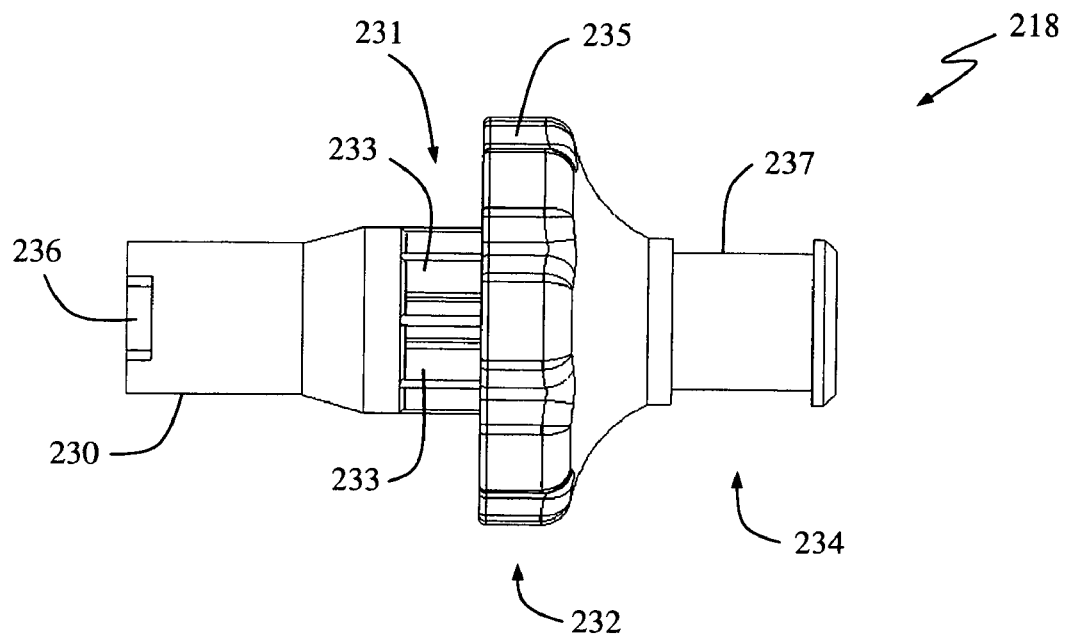
FIGS. 37-38 are side and perspective views, respectively, of a coupling element forming part of the cannula of FIG. 35.
Figure 38:
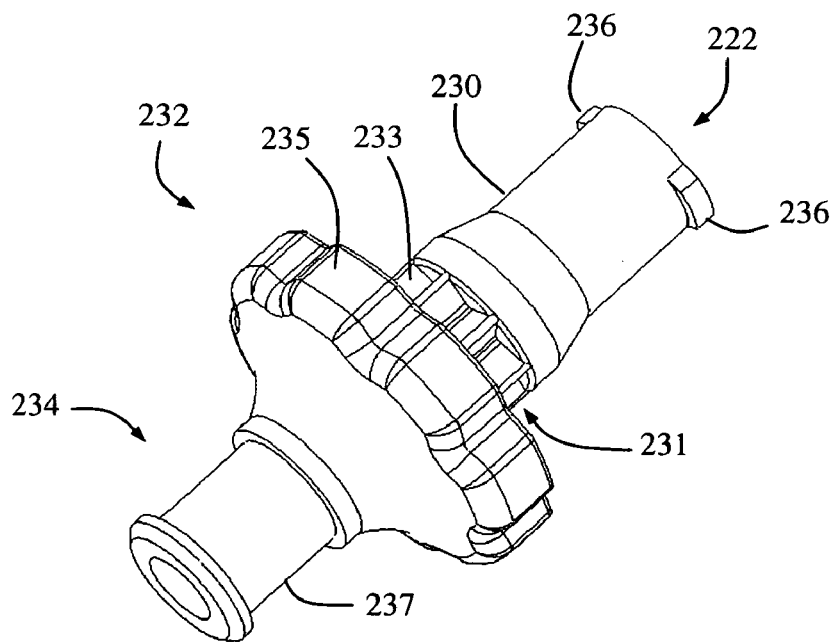

With reference to FIGS. 37-38, coupling element 218 comprises a proximal region 230, a center section 232, and a distal portion 234. Proximal region 230 includes an engagement region 231 dimensioned to engage with the handle portion 240 of the stylet 214 (as described in further detail below). The engagement region 231 may be provided in any suitable geometric configuration to allow for secure mating with the engagement tabs 144 of the handle 140. By way of example only, the coupling element 218 is shown in FIGS. 37-38 having a plurality of triangular-shaped indentations 233, however other shapes are possible. Proximal region 230 may include at least one tab member 236 that protrudes in a generally lateral direction from the proximal region 230. By way of example only, as shown in FIG. 38 proximal region 230 includes two tab members 236 positioned opposite one another and adjacent to first opening 222. Tab members 236 may be utilized to attach supplemental instruments and/or apparatuses to the cannula 212. Center section 232 may be provided with a diameter that is larger than the diameters of the proximal region 230 and distal portion 234, and may be provided with a plurality of ridges 235 and/or other features for the purpose of providing a suitable gripping area for a user. The distal portion 234 is dimensioned to engage with the elongated shaft 220 of the cannula 212 and may further be provided with a recess 237 for engagement with the sheath attachment element 292, described in further detail below.

Figure 39:
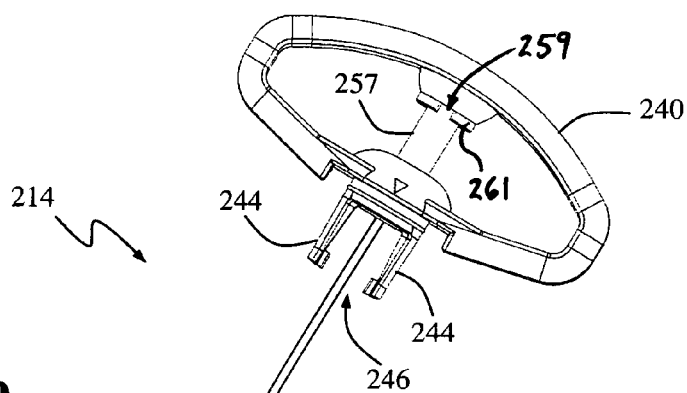
FIG. 39 is a perspective view of a stylet forming part of the pedicle access system of FIG. 31.
Figure 41:
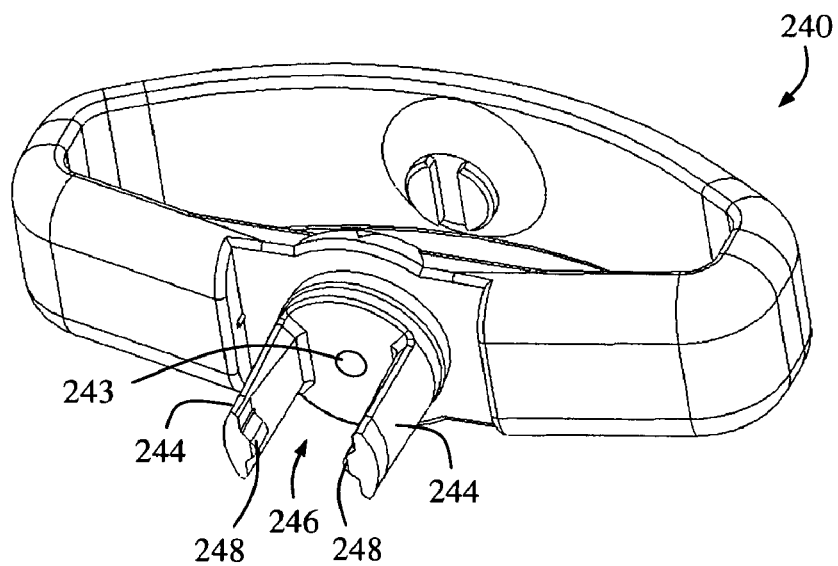
FIGS. 41-42 are perspective and plan views, respectively, of a handle forming part of the stylet of FIG. 39.
Figure 42:
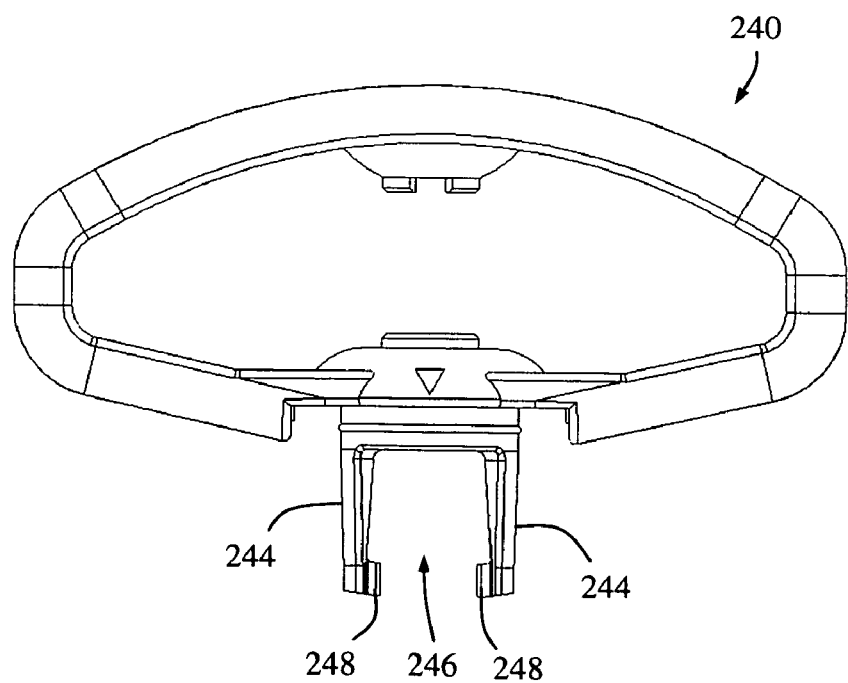

FIG. 39 illustrates an example of a stylet 214 forming part of the pedicle access system 210. Stylet 214 includes a handle portion 240 and a needle element 242. Referring to FIGS. 41-42, the handle portion 240 may (by way of example) resemble a T-handle for providing a user with a suitable gripping means. By way of example only, the handle portion 240 may have a substantially hollow interior that is not fully enclosed. Handle portion 240 includes an aperture 243 and a pair of engagement tabs 244 extending distally from handle portion 240. Aperture 243 is dimensioned to allow passage of the needle element 242 from the handle portion 240. Engagement tabs 244 extend generally perpendicularly from the handle 240 and generally parallel to one another such that the engagement tabs 244 collectively form an interior space 246. Interior space 246 is dimensioned to receive the proximal region 1230 of the coupling element 218 of the cannula 212. Each engagement tab 244 is provided with a medial (inwardly-facing) protrusion 248. Medial protrusions 248 are dimensioned to engage the engagement region 231 of the coupling element 218, described above. For this reason, the medial protrusions 248 may be provided with any geometry complementary to the shape of the engagement region 231 such that when mated, the engagement tabs 244 (via the medial protrusions 248) will prevent movement of the engagement region 231, in effect locking the cannula 212 in place relative to the stylet 214.

Figure 40:
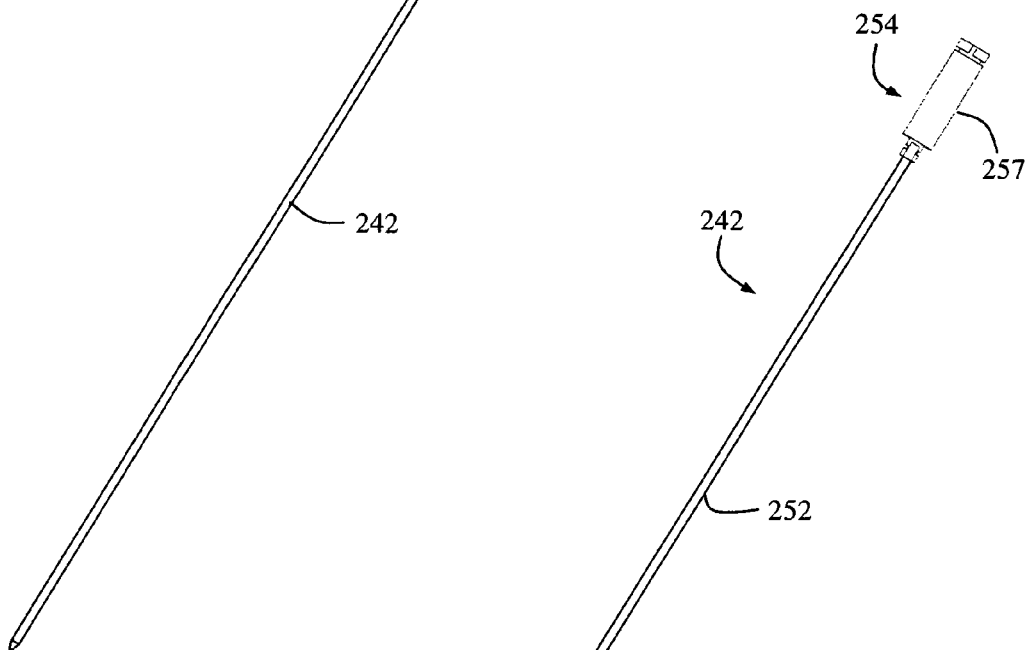
FIG. 40 is a perspective view of a needle forming part of the stylet of FIG. 39.

With reference to FIG. 40, the needle element 242 comprises an elongated shaft 252 having a proximal region 254 and a distal region 256. The proximal region 254 includes an attachment element 257 configured to attach to the interior of handle portion 240. The attachment element 257 is configured to provide a point of contact for an instrument, including but not limited to a clip attached to an electrical source and/or a device capable of detecting the position (e.g. tilt) of the assembly 210 during use. One such "tilt sensor" device is shown and described in co-pending and commonly owned U.S. Provisional Patent Application No. 60/801,488 filed May 17, 2006, the entire contents of which is hereby expressly incorporated by reference as if set forth in its entirety herein. The attachment element 257 may also include a ring element 261 located (by way of example only) at its proximal end. The ring element 261 does not extend around the entire periphery of the attachment element 257 and thereby forms a notch 259. The notch 259 is adapted to receive a male mating feature provided on the instrument (e.g. clip for attachment to electrical stimulation source and/or "tilt sensor") for the purpose of maintaining the instrument and the assembly 210 in a fixed position relative to one another. This is particularly advantageous for the "tilt sensor" device, in that the effective operation of the "tilt sensor" device is dependent upon having the "tilt sensor" maintained in a fixed position relative to the pedicle access system 210 during use. Elongated shaft 252 extends distally from proximal region 254 and generally perpendicularly from the handle 240 (and through aperture 243). Needle element 242 is dimensioned to be inserted through the interior lumen of cannula 212. The distal region 256 generally includes a distal portion of elongated shaft 252 and a shaped tip 258 having any form or shape capable of being driven into the pedicle to create a pilot hole. By way of example only, shaped tip 258 may have a beveled or double diamond form. When needle element 242 is fully inserted into cannula 212, at least a portion of distal region 256 (including shaped tip 258) may protrude slightly from the second opening 224 of cannula 212.

Needle element 242 may be composed of any conductive material, such as metal. Alternatively, needle element 242 may be composed of a non-conductive material with one or more embedded conductive elements at or near the distal end (e.g. distal region 256 and/or shaped tip 258) capable of being communicatively linked with a pedicle integrity testing system. Although shown as separate parts, the stylet 214 is preferably provided as a single unit, with the needle element 242 and attachment element 257 molded in place in the handle 240.

Figure 43:
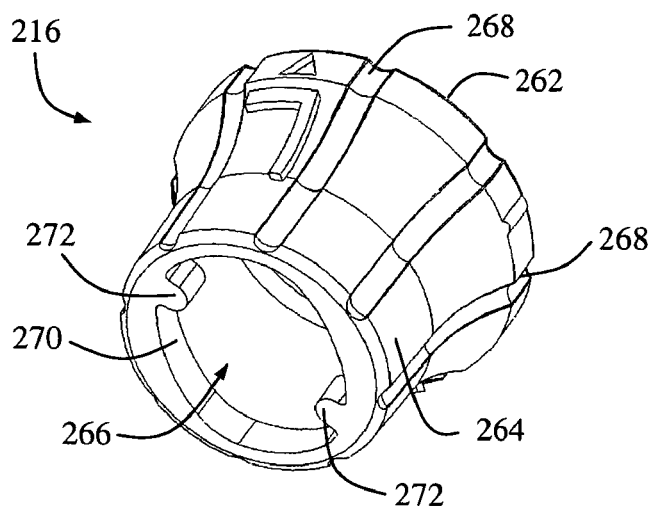
FIGS. 43-44 are perspective and plan views, respectively, of a lock collar forming part of the pedicle access system of FIG. 31.
Figure 44:
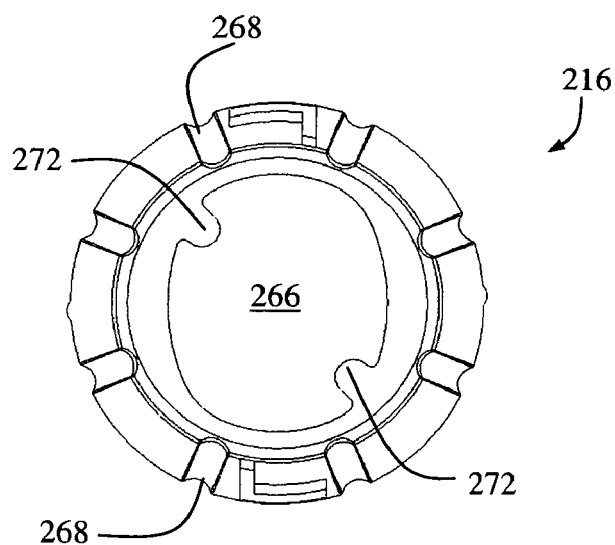

With reference to FIGS. 43-44, a lock collar 216 is provided to lockingly mate the cannula 212 and the stylet 214. Lock collar 216 has a generally cylindrical overall shape, and includes a proximal portion 262, a distal portion 264 and an interior lumen 266 extending therethrough. The proximal portion 262 may have a diameter greater than that of the distal portion 264 and is provided with a plurality of friction elements 268 to allow a user to grasp and turn the lock collar 216. The distal portion 264 includes a generally oval-shaped opening 270 providing access to the lumen 266. The opening 270 further includes a pair of opposing protrusions 272 located along the inside edge of opening 270. Protrusions 272 are located 180° from one another and are positioned approximately midway between the "long ends" and the "narrow sides" of the oval-shaped opening 270. Protrusions 272 are dimensioned to engage the sides of engagement tabs 244 of the handle 240, described above.

Figure 45:
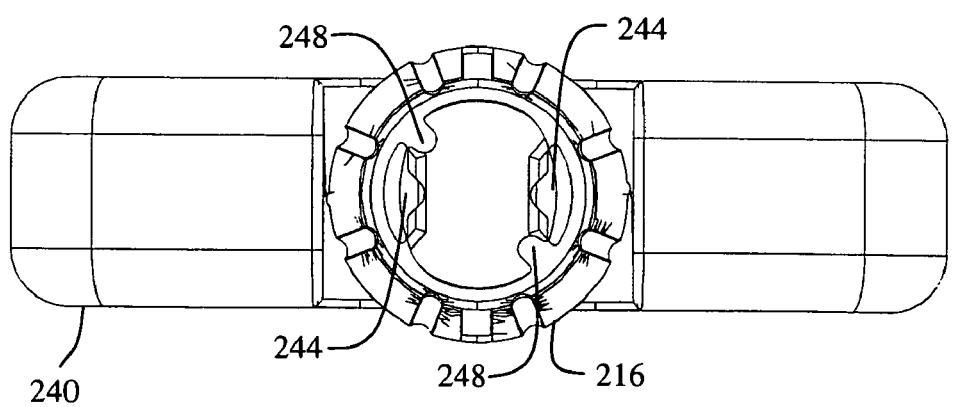
FIG. 45 is a bottom plan view of a handle of FIG. 46 in engagement with a lock collar of FIG. 43.

The interior lumen 266 is dimensioned to receive both of the engagement tabs 244 of the handle 240. Initially, the pedicle access system 210 of the present invention may be provided with the locking collar 216 attached to the stylet 214 in an initial position. This initial position is defined by the protrusions 272 resting alongside the engagement tabs 244 of the handle 240. The engagement tabs 244 at this point are disposed in the "long ends" of the oval-shaped opening 270. Upon insertion of the needle element 242 into the cannula 212, the distal region 230 of the coupling element 218 of cannula 212 will enter the space 246 of the handle 240 such that the medial protrusions 248 are aligned with (but not yet engaging) the engagement region 231 of the coupling element 218. At this point, a user would then rotate the lock collar 216 90° to a second position such that the protrusions 272 rest in against the engagement tabs 244 and the engagement tabs 244 rest in the "narrow sides" of the oval-shaped opening 270, as shown in FIG. 45. Due to the oval-shaped nature of the opening 270, upon rotation of the lock collar 216, the engagement tabs 244 will be forced toward one another, and the medial protrusions 248 will come in contact with and positively engage the engagement region 231. As noted previously, this positive engagement prevents the cannula 212 from moving. At the same time, the lock collar 216 serves to lock the engagement tabs 214 in place, effectively locking the cannula 212 and the stylet 214 together. The pedicle access system 210 is now ready for use.

Figure 47:
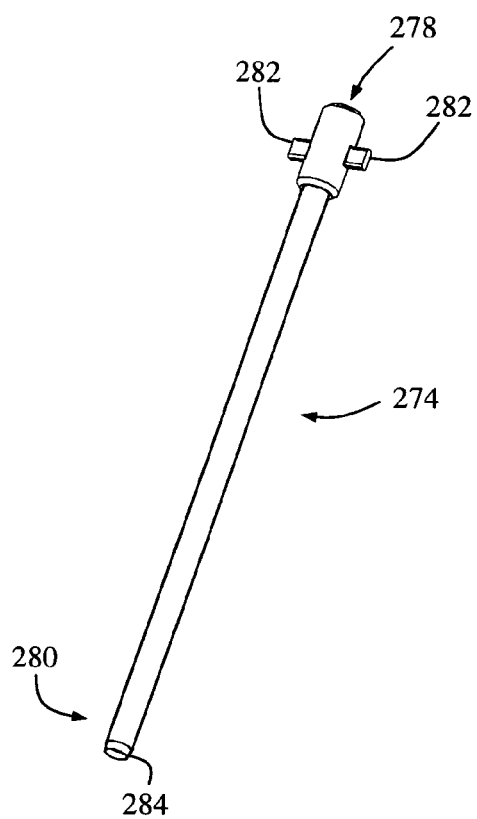
FIG. 47 is a perspective view of an insulation tube forming part of the retractable insulation sheath of FIG. 46.

As seen in FIG. 47, the insulation tube comprises a cannulated, elongated and generally cylindrical member having a proximal end 278 and a distal end 280. The proximal end 278 includes at least one tab 282 configured to slidably engage the housing member 276 as set forth below. In the example shown in FIG. 47, the insulation tube 274 includes a pair of tabs 282 positioned opposite one another, however any number of tabs 282 may be provided without departing from the scope of the invention. The distal end 280 may be provided with a generally tapered surface 284 to allow for an improved interface with the bone.

Figure 46:
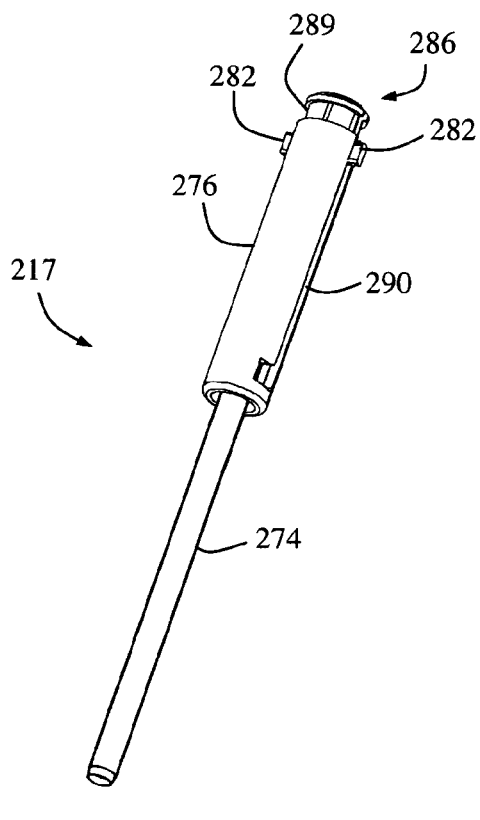
FIG. 46 is a perspective view of a retractable insulation sheath forming part of the pedicle access system of FIG. 31.
Figure 48:
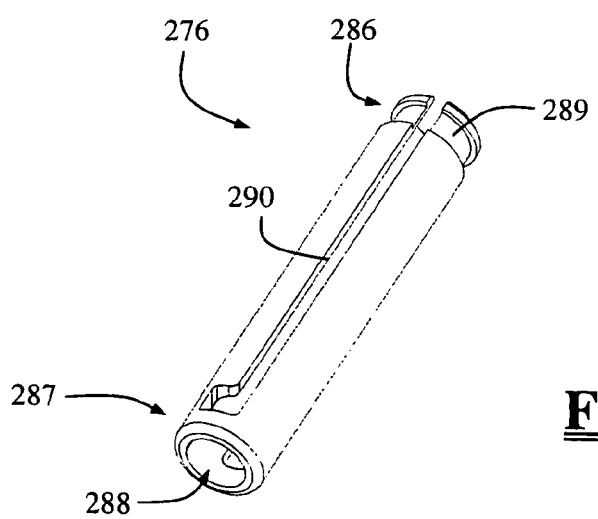
FIG. 48 is a perspective view of a retraction tube forming part of the retractable insulation sheath of FIG. 46.

Referring to FIGS. 46 & 48, the housing member 276 comprises an elongated generally cylindrical member having a proximal end 286, a distal end 287 and an interior lumen 288. The proximal end 286 includes a shaped engagement feature 289 (e.g. a recess as shown) dimensioned to engage a sheath attachment element 292 described in further detail below. The housing member 276 further includes at least one elongated track 290 in the form of a cutout section extending substantially the length of the housing member 276. The track 290 is dimensioned to slidably receive the tabs 282 of the insulation tube 274 such that the insulation tube 274 is allowed to migrate within the lumen 288.

Figure 49:
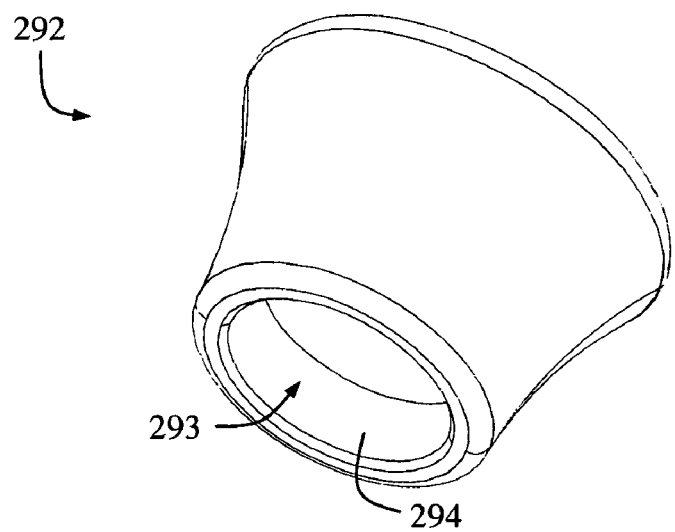
FIGS. 49-50 are perspective views of a sheath attachment element forming part of the pedicle access system of FIG. 31.
Figure 50:
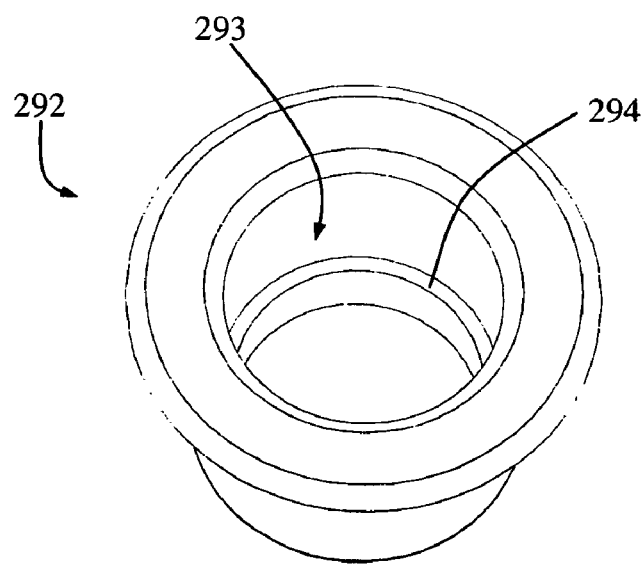

With reference to FIGS. 49-50, an example of a sheath attachment element 292 is shown. The sheath attachment element 292 may be provided as a generally cylindrical member having an interior lumen 293. Sheath attachment element 292 is dimensioned to provide a snap-fit engagement with both the housing member 276 and the coupling element 218 of cannula 212. The lumen 293 is provided with a first ridge 294 near a distal end for secure engagement with recess 289 of the housing member 276. Similarly, the lumen 293 is provided with a second ridge (not shown) near a proximal end for engagement with recess 237 of the coupling element 218 (FIG. 37). During assembly of the pedicle access system 210, the retractable insulation sheath 217 may be provided with the sheath attachment element 292 mated to the housing member 276. The cannula 212 is then inserted into the insulation sheath 217 and sheath attachment element 292 will then engage the coupling element 218, thus securely attaching the insulation sheath 217 to the pedicle access system 210.

Figure 32:
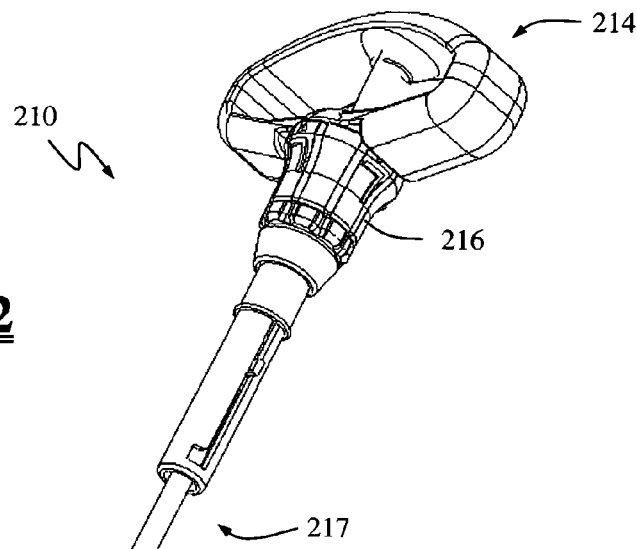
FIGS. 32-33 are perspective views of an assembled pedicle access system of FIG. 31.
Figure 33:
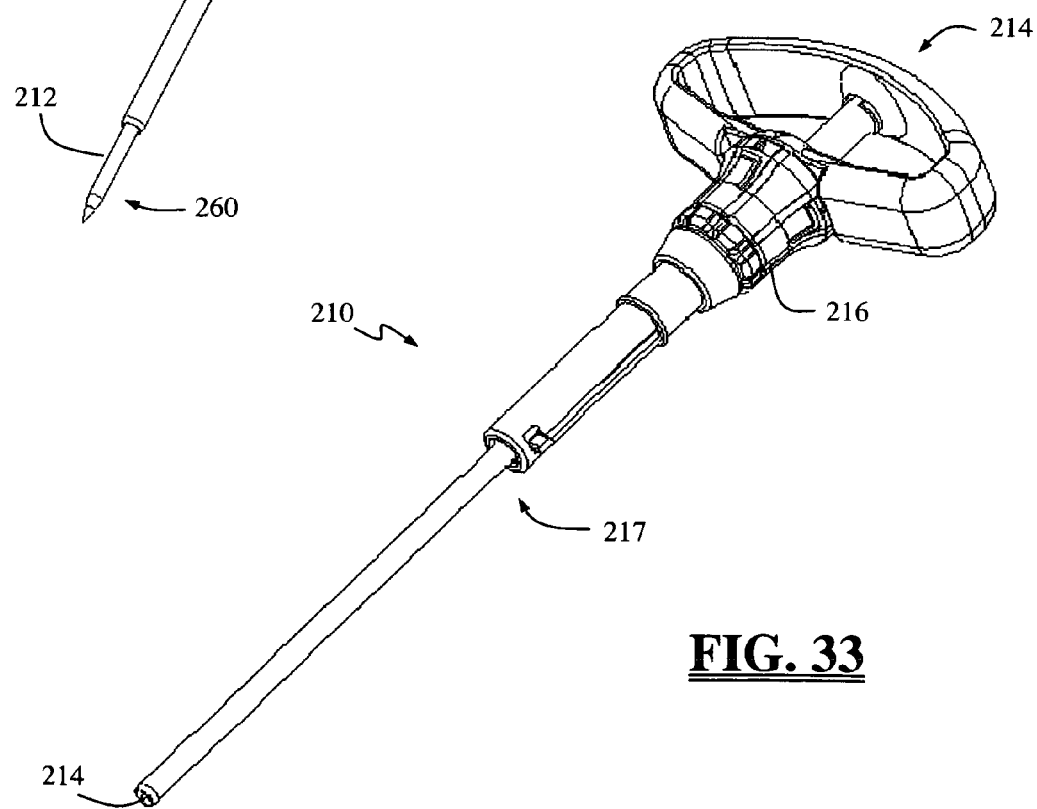
Figure 34:
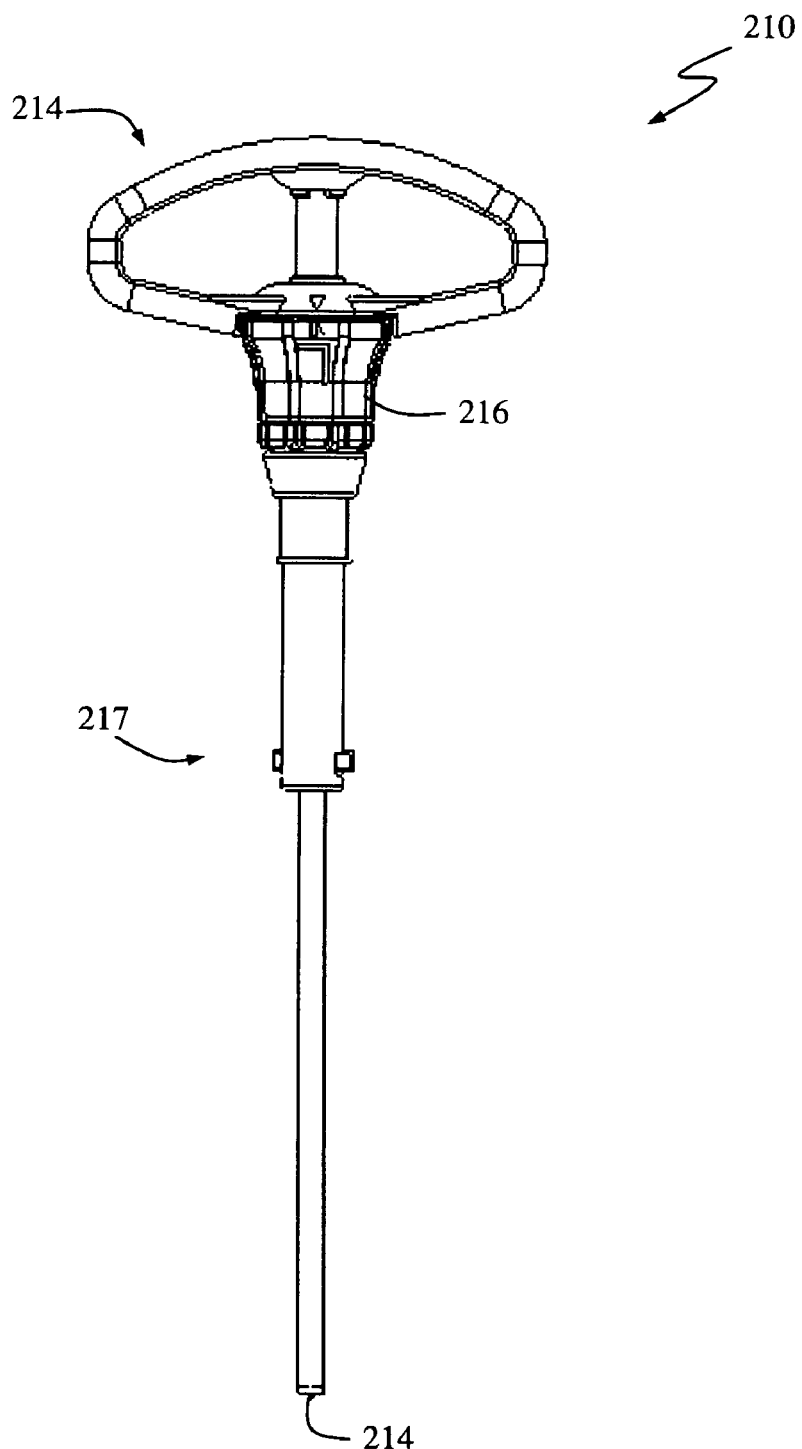
FIG. 34 is a front view of the pedicle access system of FIG. 32.

In use, the pedicle access system 210 is provided with the insulation tube 274 in a first, fully extended position (e.g. FIG. 33). The insulation tube 274 will remain in this position as the pedicle access system 210 is advanced through an operative corridor to a bony target site (e.g. a pedicle). Upon initial engagement with the bony structure, the tip 258 of the needle element 242 and the distal end 280 of the insulation tube 274 may contact the bone at approximately the same time. At this point the user may want to begin monitoring the integrity of the pilot hole formation by using a stimulation signal as described below. As the needle 242 is advanced into the bone, forming a pilot hole, the distal end 280 remains engaged to the outside surface of the bone. At the same time, the proximal end 278 (including tabs 282) of the insulation tube will advance proximally along the track 290 of the housing member 276. Due to the insulated nature of insulation tube 274, the portion of needle element 242 and cannula 212 that protrude from insulation tube 274 effectively constitute a stimulation region 260 (FIG. 32). As the needle 242 and cannula 212 are advanced into the bony structure (and the insulation tube 274 remains on the outside of the bony structure), the stimulation region 260 becomes larger. Upon completion of the pilot hold formation, the needle 242 and cannula 212 are withdrawn from the bony structure, and the pedicle access system 210 may be removed from the operative corridor. A spring (not shown) or other control mechanism may be provided to limit the extent of migration of the insulation tube 274 and/or provide a means for the insulation tube 274 to bias toward returning to the fully extended position upon removal of the needle 242 from the pilot hole in the pedicle.

In an optional embodiment of the present invention, the tubular insulation member 274 may be biased into an "automatically extended" manner, such as providing a spring member 219 (shown in FIG. 31) in between a proximal end member 278 of the tubular insulation member 274 and the housing member 276, both of which will be described in greater detail below. By positioning the spring member 219 in this manner, the distal end of the spring member 219 will abut into the tab elements 282 (FIG. 47) while the proximal end of the spring member 219 will abut a portion within the housing member 276 (preferably at or near the proximal region of the housing member 276). This will, in turn, automatically force the tubular insulation member 274 away from housing member 276. The spring member 219 preferably has a suitable modulus of elasticity such that it will readily compress to allow the tubular insulation member 274 to be received within the housing member 276 while the stylet 242 is being advanced into the target bone, and expand to its original shape to allow the tubular insulation member 274 to again fully extend from the housing member 276 when the stylet 242 is being withdrawn from the target bone.

Figure 51:
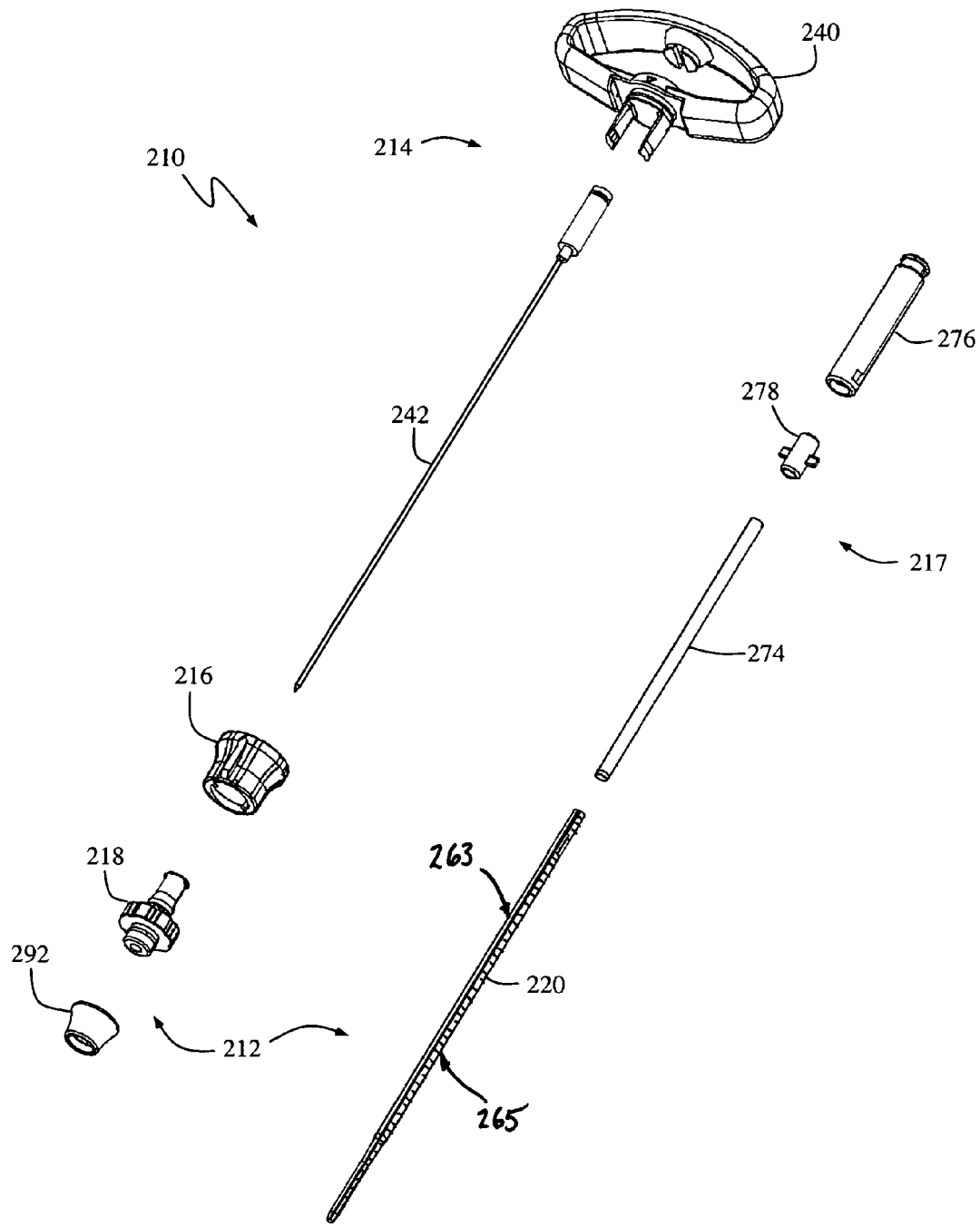
FIG. 51 is an exploded perspective view of a pedicle access system according to a further alternative embodiment of the present invention providing directionality during use.

With reference to FIGS. 51-53, a still further optional embodiment of the present invention is shown wherein the elongated shaft 220 of the cannula 212 is provided with an insulated region 263 and a non-insulated region 265 to provide directionality during use. More specifically, the non-insulated region 265 is conductive during use and transmits the stimulation signal to the surrounding tissue (e.g. bone), while the insulated region 263 is non-conductive and does not transmit the stimulation signal during use. A user may rotate the elongated shaft 220 during stimulation and, by knowing the location of the non-insulated region 265, gauge the location of any potential breach. More specifically, if a breach or near breach exists in the medial wall of the pedicle, the readings from the neurophysiologic monitoring system will decrease as the non-insulated region 265 is pointed in the direction of the medial wall and will increase as the non-insulated region 265 is pointed away from the medial wall. In addition to detecting a breach or partial breach, the directionality of this embodiment may also be used to detect the location of the elongated shaft 220 within the pedicle itself (e.g. whether it's centered or not) using the same principle. That is, if the neurophysiologic readings are approximately equal as the non-insulated region 265 is rotated during stimulation, it would indicate that the elongated shaft 220 is generally centered within the pedicle. If the readings vary during rotation, it may indicate that the elongated shaft 220 is not centered, such that the surgeon may wish to reposition the elongated shaft until the readings upon rotation are approximately equal. As shown in FIG. 53A (which is a cross section along lines 53A-53A in FIG. 53), the non-insulated region 265 be provided having any number of different sizes relative to the overall circumference of the elongated shaft 220, such as a fraction (top of FIG. 53A), approximately half (middle of FIG. 53A) or a majority (bottom of FIG. 53A).

Figure 54:
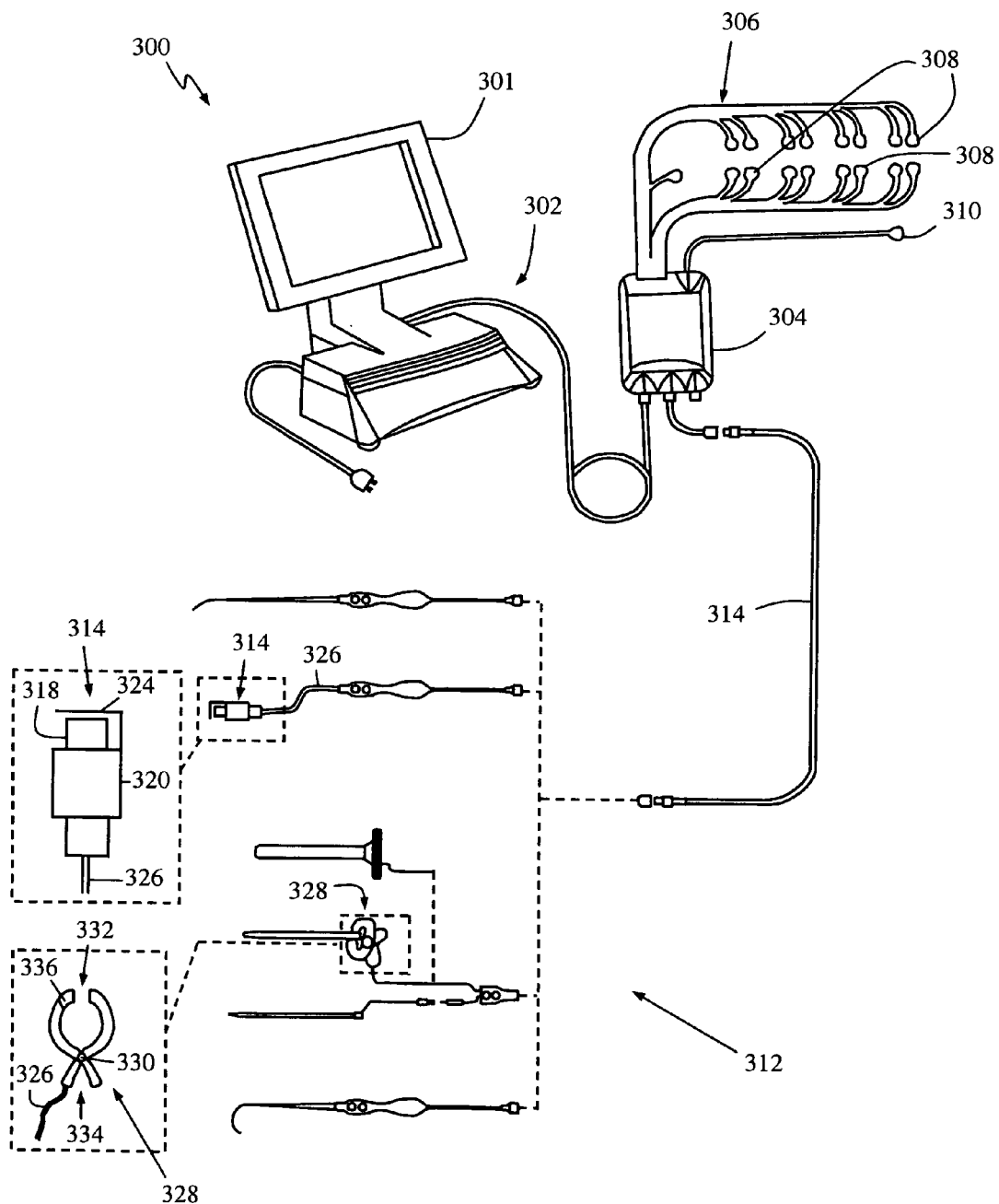
FIG. 54 is a perspective view of an example of a neurophysiology system capable of connecting to the pedicle access systems of FIGS. 1, 19 and 31 to conduct pedicle integrity tests.

In a significant aspect of the present invention, the pedicle access systems 10, 110 and 210 described above may be used in combination with neurophysiology monitoring systems and methods to conduct pedicle integrity assessments while achieving initial access to the pedicle. By way of example only, the pedicle access systems 10, 110 and 210 may be used in combination with the system and methods shown and described in commonly owned and co-pending Int'l Patent App. Ser. No. PCT/US02/22247, filed on Jul. 11, 2002, the contents of which are hereby incorporated by reference into this disclosure as set forth herein in its entirety. With reference to FIG. 54, an example of one such neurophysiology system 300 includes a display 301, a control unit 302, a patient module 304, an EMG harness 306, including eight pairs of EMG electrodes 308 and a return electrode 310 coupled to the patient module 304, and a host of surgical accessories 312, including an electric coupling device 316 capable of being coupled to the patient module 304 via one or more accessory cables 314.

The neurophysiology system 300 performs pedicle integrity assessments by determining the amount of electrical communication between a stimulation signal and the adjacent nerve root. To do this, a stimulation signal is applied to the pilot hole or pedicle screw via one of the surgical accessories 312. The EMG electrodes 308, positioned over the appropriate muscles, measure the EMG responses corresponding to the stimulation signal. The relationship between the EMG response and the stimulation signal is then analyzed by the system and the results are conveyed to the user on the display 301. The basic theory underlying the pedicle integrity test is that given the insulating character of bone, a higher stimulation current (or current density) is required to evoke an EMG response when the stimulation signal is applied to an intact pedicle as opposed to a breached pedicle. Thus, if EMG responses are evoked by stimulation currents (or current densities) lower than a predetermined safe level, the surgeon may be alerted that there is a possible breach. The neurophysiology system may be provided with software capable of compensating for multiple safe stimulation thresholds based on different current densities being applied to the pedicle by certain geometries of different instruments.

The pedicle access systems 10, 110 and 210 described above may be combined to and used in conjunction with the neurophysiology system 300 by attaching (not shown) the electric coupling device 314 to (for example) the non-insulated region 28 of the cannula 12 of pedicle access system 10. The electric coupling device 314 may comprise a number of possible embodiments which permit the device to attach and hold a surgical tool (such as the pedicle access system 10) while allowing transmission of a stimulation signal to the tool. One such electric coupling device 314 utilizes a spring-loaded plunger to hold the surgical tool and transmit the stimulation signal. The plunger 318 is composed of a conductive material such as metal. A nonconductive housing 320 partially encases the plunger rod 318 about its center. Extending from the housing 320 is an end plate 324. An electrical cable 326 connects the electric coupling device 314 to neurophysiology system 300. A spring (not shown) is disposed within the housing 320 such that in a natural or "closed" state the plunger 318 is situated in close proximity to the endplate 324. Exerting a compressive force on the spring (such as by pulling the cable 326 while holding the housing 320) causes a gap between the end plate 324 and the plunger 318 to widen to an "open" position, thereby allowing insertion of a surgical tool between the end plate 324 and plunger 318. Releasing the cable 326 allows the spring to return to a "closed" position, causing the plunger 318 to move laterally back towards the endplate such that a force is exerted upon the surgical tool and thereby holds it in place between the endplate 324 and the plunger 318. Thereafter the electrical stimulus may be passed from the neurophysiology system 300 through the cable 326 and plunger 318 to the surgical tool.

Alternatively, the electrical coupling device may be embodied in the form of a clip 328. The clip 328 is comprised of two prongs hingedly coupled at a coupling point 330 such that the clip 328 includes an attachment end 332 and a non-attachment end 334. A stimulation electrode 336 is disposed on the attachment end 332 and communicates with an electric cable 326 extending from the non-attachment end 334 to the neurophysiology system 300. In a "closed" position the prong ends at the attachment end 332 touch. Depressing the prongs at the non-attachment end 334 in a direction towards each other causes a gap to form between the prong ends at the attachment end 332. Positioning the "opened" attachment end 332 over a desired surgical tool (such as the pedicle access system 10) and releasing the force on the non-attachment end 334 causes the attachment end 332 to pinch tight on the surgical tool and thereby allow the electrical stimulus to pass from neurophysiology system, through the stimulation electrode 336, to the surgical tool.

The pedicle access system 10 may thus be used to safely access the pedicle and safely form a pilot hole. To do this, the cannula 12, stylet 14, and T-handle 16 are preferably all combined and locked together as described above. Using the T-handle 16 to control the movement and positioning of the pedicle access system 10, the surgeon may position the stimulation point on the desired target site. Next, the electric coupling device 116 may be attached to the uninsulated region 28 of cannula 12 and the T-handle 16 may be removed to facilitate the use of a tool such as a needle driver. Stimulation signals are delivered to the pedicle access system 10 and emitted from the stimulation region 60 as it is being driven in to the bone, forming the pilot hole. Should the neurophysiology system 300 report a potential breach of the pedicle, pilot hole formation may be halted and any steps deemed to be necessary by the surgeon, based on his or her professional judgment, may be taken to correct the problem. Alternatively, the electric coupling device 316 may be attached before positioning the pedicle access system 10, and the neurophysiology system 300 may be employed to monitor the proximity of any nerves during positioning.

In another significant aspect of the present invention, the pedicle access system 10 may be used in conjunction with spinal fixation systems that require access to pedicle target sites and need pilot holes, including but not limited to those systems shown and described in commonly owned and co-pending U.S. patent application Ser. No. 11/031,506 filed Jan. 6, 2005, and commonly owned and co-pending Int'l Patent App. Ser. No. PCT/US05/032300 filed Sep. 8, 2005. After positioning the pedicle access system 10 on the desired pedicle target site and safely forming a pilot hole as described above, the T-handle 16 and stylet 14 may be unlocked and removed from the cannula 12, leaving the cannula 12 positioned in the pilot hole. Guide wires subsequently used by the spinal fixation systems may then be safely deployed to the pilot hole through the cannula 12. Once the guide wire is in position the cannula 12 may be removed from the target site and the surgeon may commence use of the surgical fixation system.

While the invention is susceptible to various modification and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the scope and spirit of the invention as defined herein.

What is claimed is:

1. A system for use in a medical procedure, comprising:
    an access needle, including:
        an elongated needle element having a shaped tip advanceable into a bony structure of a patient's spine;
        an elongated cannula lockingly mateable with said needle element and having a lumen to slidably receive said needle element therethrough such that said shaped tip of said needle element extends distally beyond a distal end of said cannula;
        an insulative sheath disposed about the exterior of said cannula, wherein said insulative sheath is coupled to an attachment element situated near a proximal end of said cannula, the attachment element including an exterior surface defining a lumen enclosing a distal portion of the cannula and a distal portion of the insulative sheath, the attachment element including at least one longitudinally running slot and the proximal portion of the insulative sheath including at least one tab extending into the slot;
        a locking mechanism that selectively locks said needle element and said cannula together when said needle element is fully received in said cannula; and
        a handle attachable to at least one of said needle element and said cannula;
    wherein said access needle has a contact element coupleable to a source of electrical stimulation and in electrical communication with at least one of said shaped tip and said distal end of said cannula such that a stimulation signal is deliverable to a target region of said bony structure to perform a pedicle integrity assessment when said access needle is in contact with said bony structure.

2. The system of claim 1, wherein said handle is removable.

3. The system of claim 1, wherein said contact element is a conductive surface on at least one of said needle element, cannula, and handle, said contact element being engageable by a stimulation clip comprising said stimulation source.

4. The system of claim 1, wherein said insulative sheath is slidable along the exterior of said cannula between a first position and a second position.

5. The system of claim 1, wherein a distal end of said insulative sheath is adapted to engage a surface of said bony structure when said needle element and cannula are advanced into said bony structure such that said insulative sheath slides relative to said cannula as said needle element and cannula are advanced deeper into said bony structure exposing the exterior of said cannula to the interior of the bony structure.

6. The system of claim 1, wherein said insulative sheath is biased to a first position in which the exterior of the cannula is least exposed.

7. The system of claim 1, wherein said locking mechanism comprises a lock collar.

8. The system of claim 1, wherein said handle is adapted to matingly engage an instrument in a fixed position relative to said handle.

9. The system of claim 8, wherein said instrument is at least one of a clip to couple said access needle to said source of electrical stimulation and a sensor for monitoring the angular orientation of the access needle during use.

10. A surgical instrument, comprising:
    an elongated needle element including a shaped tip advanceable into a bony structure of a patient's spine;
    a handle coupled to said needle element to facilitate manipulation of said surgical instrument via a user;
    a cannula having a lumen that slidably receives said needle element therein, the cannula having an exterior that is insulated over a majority of the length of said cannula, and wherein said needle element and said cannula are lockingly engageable when said needle element is fully received within said cannula; and
    an insulative sheath slidable along the exterior of said cannula between a first position and a second position wherein said insulated sheath is coupled to an attachment element situated near a proximal end of the cannula, the attachment element including an exterior surface defining a lumen enclosing a distal portion of the cannula and a distal portion of the insulative sheath, the attachment element including at least one longitudinally running slot and the proximal portion of the insulative sheath including at least one tab extending into the slot; and
    wherein at least one of said cannula and said handle includes a contact element in electrical communication with at least one of said shaped tip of said needle element and a distal end of said cannula, said contact element being coupleable with an electrical source to transmit an electrical stimulation current from said electrical source to said at least one of said shaped tip of said needle element and said distal end of said cannula and into a hole formed in said bony structure by said instrument.

11. The surgical instrument of claim 10 wherein a locking collar is utilized to lockingly engage said needle element and said cannula.

12. The surgical instrument of claim 10, wherein said insulative sheath is biased to a first position in which the exterior of the cannula is least exposed.

13. The surgical instrument of claim 10, wherein said insulated sheath is spring biased to the first position in which the exterior of the cannula is least exposed.

14. A system for use in a medical procedure, comprising: an access needle including:
- an elongated needle element having a shaped tip advanceable into a bony structure of a patient's spine;
- an elongated cannula lockingly mateable with said needle element and having a lumen to slidably receive said needle element therethrough such that said shaped tip of said needle element extends distally beyond a distal end of said cannula;
- an insulative sheath disposed about the exterior of said cannula, wherein said insulative sheath is coupled to an attachment element, said attachment element defining a lumen enclosing a portion of said cannula and a portion of said insulative sheath, said attachment element including at least one longitudinally running slot and the proximal portion of said insulative sheath including at least one tab extending through said slot;
- a locking mechanism that selectively locks said needle element and said cannula together when said needle element is fully received in said cannula; and
- a handle attachable to at least one of said needle element and said cannula;

wherein said access needle is coupleable to a source of electrical stimulation and in electrical communication with at least one of said shaped tip and said distal end of said cannula such that a stimulation signal is deliverable to a target region of said bony structure to perform a pedicle integrity assessment when said access needle is in contact with said bony structure.

15. The system of claim 14, wherein said handle is removable.

16. The system of claim 14, wherein a conductive surface on at least one of said needle element, cannula, and handle, is engageable by a stimulation clip comprising said stimulation source.

17. The system of claim 14, wherein said insulative sheath is slidable along the exterior of said cannula between a first position and a second position.

18. The system of claim 14, wherein the distal end of said insulative sheath is adapted to engage a surface of said bony structure when said needle element and cannula are advanced into said bony structure such that said insulative sheath slides relative to said cannula as said needle element and cannula are advanced deeper into said bony structure exposing the exterior of said cannula to the interior of the bony structure.

19. The system of claim 14, wherein said insulative sheath is biased to a first position in which the exterior of the cannula is least exposed.

20. The system of claim 14, wherein said locking mechanism comprises a lock collar.

21. The system of claim 14, wherein said handle is adapted to matingly engage an instrument in a fixed position relative to said handle.

22. The system of claim 21, wherein said instrument is at least one of a clip to couple said access needle to said source of electrical stimulation and a sensor for monitoring the angular orientation of the access needle during use.

23. A system for use in a medical procedure, comprising: an access needle including:
- an elongated needle element having a shaped tip advanceable into a bony structure of a patient's spine;
- an elongated cannula lockingly mateable with said needle element and having a lumen to slidably receive said needle element therethrough such that said shaped tip of said needle element extends distally beyond a distal end of said cannula;
- an insulative sheath disposed about the exterior of said cannula, wherein said insulative sheath is spring-biased to a first position in which the exterior of the cannula is least exposed;
- a locking mechanism that selectively locks said needle element and said cannula together when said needle element is fully received in said cannula; and
- a handle attachable to at least one of said needle element and said cannula;

wherein said access needle is coupleable to a source of electrical stimulation and in electrical communication with at least one of said shaped tip and said distal end of said cannula such that a stimulation signal is deliverable to a target region of said bony structure to perform a pedicle integrity assessment when said access needle is in contact with said bony structure.

24. The system of claim 23, wherein said handle is removable.

25. The system of claim 23, wherein a conductive surface on at least one of said needle element, cannula, and handle, is engageable by a stimulation clip comprising said stimulation source.

26. The system of claim 23, wherein said insulative sheath is slidable along the exterior of said cannula between said first position and a second position.

27. The system of claim 23, wherein a distal end of said insulative sheath is adapted to engage a surface of said bony structure when said needle element and cannula are advanced into said bony structure such that said insulative sheath slides relative to said cannula as said needle element and cannula are advanced deeper into said bony structure exposing the exterior of said cannula to the interior of the bony structure.

28. The system of claim 23, wherein said insulative sheath is coupled to an attachment element, the attachment element defining a lumen enclosing a portion of the cannula and a distal portion of the insulative sheath, the attachment element including at least one longitudinally running slot and the proximal portion of the insulative sheath including at least one tab extending into said slot.

29. The system of claim 23, wherein said locking mechanism comprises a lock collar.

30. The system of claim 23, wherein said handle is adapted to matingly engage an instrument in a fixed position relative to said handle.

31. The system of claim 30, wherein said instrument is at least one of a clip to couple said access needle to said source of electrical stimulation and a sensor for monitoring the angular orientation of the access needle during use.

* * * * *